United States Patent
Miyazono et al.

(10) Patent No.: US 6,692,925 B1
(45) Date of Patent: Feb. 17, 2004

(54) PROTEINS HAVING SERINE/THREONINE KINASE DOMAINS, CORRESPONDING NUCLEIC ACID MOLECULES, AND THEIR USE

(75) Inventors: Kohei Miyazono, Shiki (JP); Takeshe Imamura, Tokyo (JP); Peter ten Dijke, Amsterdam (NL)

(73) Assignee: Ludwig Institute for Cancer Research, New York, NY (US)

(*) Notice: Subject to any disclaimer, the term of this patent is extended or adjusted under 35 U.S.C. 154(b) by 0 days.

(21) Appl. No.: 09/267,963

(22) Filed: Mar. 12, 1999

Related U.S. Application Data

(63) Continuation-in-part of application No. 09/039,177, filed on Mar. 13, 1998, now abandoned, which is a continuation-in-part of application No. 08/436,265.
(60) Provisional application No. PCT/GB93/02367, filed on Nov. 17, 1993, now Pat. No. 6,316,217.

(30) Foreign Application Priority Data

| Nov. 17, 1992 | (GB) | 9224057 |
| Mar. 8, 1993 | (GB) | 9304677 |
| Mar. 8, 1993 | (GB) | 9304680 |
| May 28, 1993 | (GB) | 9311047 |
| Jul. 2, 1993 | (GB) | 9313763 |
| Aug. 3, 1993 | (GB) | 9316099 |
| Oct. 15, 1993 | (GB) | 9321344 |

(51) Int. Cl.$^7$ .................. G01N 33/53; C07K 14/495; C07K 16/22; C07K 16/28; C12P 21/02

(52) U.S. Cl. .............. 435/7.2; 435/7.21; 435/69.1; 435/69.7; 435/325; 530/350; 530/388.22; 530/388.23; 530/387.1; 530/389.2

(58) Field of Search .................. 435/7.1, 7.2, 7.21, 435/7.6, 69.1, 69.7, 325; 530/350, 387.1, 388.22, 388.23, 389.2

(56) References Cited

U.S. PATENT DOCUMENTS

| 5,521,295 A | 5/1996 | Pacifici et al. |
| 5,538,892 A | 7/1996 | Donahue et al. |
| 5,614,609 A | 3/1997 | Ibanez et al. |

FOREIGN PATENT DOCUMENTS

| WO | 9514778 | 11/1993 |
| WO | 9507982 | 3/1995 |
| WO | WO-97-07135 A | 2/1997 |

OTHER PUBLICATIONS

Takahashi et al. Effects of lipoprotein(a) and low density lipoprotein on growth of mitogen–stimulated human umbilical vein endothelial cells. Atherosclerosis, (Feb. 1996) 120 (1–2) 93–9.*

Hopkins et al. Mediators of induction of augmented expression of plasminogen activator inhibitor type–1 in Hep G2 cells by platelets. Thrombosis and Haemostasis, (Aug. 1, 1991) 66 (2), Abstract Only.*

Kokame et al. Homocysteine–respondent genes in vascular endothelial cells identified by differential display analysis. GRP78/BiP and novel genes. Journal of Biological Chemistry, (Nov. 22, 1996) 271 (47) 29659–65.*

Hopkins et al. Mediators of induction of augmented expression of plasminogen activator inhibitor type–1 in Hep G2 cells by platelets. Thrombosis and Haemostasis, (Aug. 1, 1991) 66 (2), 239–245.*

Kurihara et al. The possible role of endothelin–1 in the pathogenesis of coronary vasospasm. Journal of Cardiovascular Pharmacology, (1989) 13 Suppl 5 S132–7.*

Attisano et al., *Cell*, 68–97–108 (1992).
Cate et al., *Cell*, 45:685–698 (1986).
Chiefetz et al., *J. Biol. Chem.*, 267:19027–19030 (1992).
Cunningham et al., *Proc. Natl. Acad. Sci. USA*, 89:11740–11744 (1992).
Ebner et al., *Science*, 260:1344–1348 (1993).
Eto et al., *Biochem. Biophys. Res. Comm.*, 142:1095–1103 (1987).
Georgi et al., *Cell*, 61:635–645 (1990).
Hino et al., *J. Biol. Chem.*, 264:10309–10314 (1989).
Laiho et al., *J. Biol. Chem.*, 266:9100–9112 (1991).
Lin et al., *Cell*, 68:775–785 (1992).
Lin et al., *Science*, 260:1130–1132 (1993).
Lopez–Casillas et al., *Cell*, 73:1435–1444 (1993).
Massague, *Cell*, 69:1067–1070 (1992).
Mattews et al., *Science*, 255:1702–1705 (1992).
Matthews et al., *Cell*, 65:973–982 (1991).
Matthews et al., *Cell*, 68:775–785 (1991).
Moses et al., *Cell*, 63:245–247 (1990).
Murata et al., *Proc. Natl. Acad. Sci. USA*, 85:2434–2438 (1988).
Paralkar et al., *J. Cell. Biol.*, 119:1721–1728 (1992).
Paralkar et al., *Proc. Natl. Acad. Sci. USA*, 87:8913–8917 (1991).
Roberts and Sporn, "Peptide Growth Factors and Their Receptors", Sporn and Roberts eds., Pt. 1., Berlin: Springer–Verlag, 419–472 (1990).
Segarini et al., *Mol. Endo.*, 3:261–272 (1989).
Smith et al., *Nature*, 345:729–731 (1990).
Vale et al., "Peptide Growth Factors and Their Receptors", Sporn and Roberts eds., Pt. 2., Berlin: Springer–Verlag, 211–248 (1990).
van den Eijnden–Van Raaij et al., *Nature*, 345–732–734 (1990).

(List continued on next page.)

Primary Examiner—David Romeo
(74) Attorney, Agent, or Firm—Fulbright & Jaworski L.L.P.

(57) ABSTRACT

The invention relates to the molecule referred to as ALK-1, and its role as a type I receptor for members of the TGF-β family. The molecule has a role in the phosphorylation of Smad-5 and Smad1, which also act as activators of certain genes. Aspects of the invention relate to this interaction.

7 Claims, 11 Drawing Sheets

OTHER PUBLICATIONS

Wang et al., *Cell*, 67:797–805 (1991).

Wozney et al., *Science*, 242:1528–1534 (1988).

Wrana et al., *Cell*, 71:1003–1004 (1992).

Kretzschmar M et al. "Smads: Mediators and Regulators of TGF–Beta Signaling" Current Opinion in Genetics & Development, Current Biology Ltd., XX, 8(8), pp. 103–111, Feb. 1998.

Persson U et al. "Transforming Growth Factor (TGF–Beta)–Specific Signaling by Chimeric TGF–Beta Type II Receptor with Intracellular Domain of Activin Type IIB Receptor" Journal of Biological Chemistry 272(34), pp. 21187–21194, Aug. 1997.

Lechleider R J et al. "Serine Phosphorylation, Chromosomal Localization, and Transforming Growth Factor–Beta Signal Transduction by Human BSP–1", Journal of Biological Chemistry 271 (30), pp. 17617–17620, Jul. 1996.

Yingling J M et al. "Mammalian dwarfins are phosphorylated in response to transforming growth factor beta and are implicated in control of cell growth" Proceedings of the National Academy of Sciences of the United States of America. 93(17), pp. 8940–8944, Aug. 1996.

Dijke Ten P et al. "Characterization of Type I Receptors for Transforming Growth Factor–B and Activin" Science, American Association for the Advancement of Science, 264(5155), pp. 101–104, Apr. 1994.

Kretzschmar M et al. "The TGF–Beta Family Mediator Smad1 is Phosphorylated Directly and Activated Functionally by the BMP Receptor Kinase" Genes and Development, Cold Spring Harbor, (11(8), pp. 984–995, Apr. 1997.

Takase M et al. "Induction of Smad6 mRNA by Bone Morphogenitic Proteins" Biochemical and Biophysical Research Communications. 244(1), pp. 26–29, Mar. 1998.

Feng X H et al. "A Kinase Subdomain of Transforming Growth Factor–Beta (TGF–Beta) Type I Receptor Determines the TGF–Beta Intracellular Signaling Specificity" The Embo Journal 16(13), pp. 3912–3923, Jul. 1997.

Attisano L et al. "Identification of Human Activin and TGFBeta Type I Receptors That Form Heteromeric Kinase Complexes With Type II Receptors", Cell, Cell Press, 75, pp. 671–680, Nov. 1993.

Basson, CT et al. J. Cell Physiology 153: 118–128 (1992.

Heldin, C–H.H et al. Nature 390:465–471 (1997).

\* cited by examiner

FIG. 1

```
cons.aa              G   G   G V          A K                       E
hTGFBR-II   LDTLVGKGRFAEVYKAKLKQNTSEQFETVAVKIFPYDHYASWKDRKDIFSDINLKHENILQF
mActR-IIB   LLEIKARGRFGCVWKAQLMN------DFVAVKIKPLQDKQSWQSEREIFSTPGMKHENLLQF
mActR-II    LLEVKARGRFGCVWKAQLLN------EYVAVKIFPIQDKQSWQNEYEVYSIPGMKHENILQF
daf-1       LTGRVGSGRFGNVSRGDYRG------EAVAVKVFNAIDEPAFHKEIEIFETRMLRHPNVLRY
subdomains          I                 II              III            IV hTGFBR-II   LTAEERKTELGKQYWLITAFHAKGNLQEYLTRHVISWEDLRNVGSSLARGLSLSHLHSDHTP-C
mActR-IIB   IAAEKRGSNLEVELWLITAFHDKGSLIDYLKGNIITWNELCHVAETMSRGISYLHEDVPWCR
mActR-II    IGAEKRGTSVDVDLWLITAFHEKGSLSDFLKANVVSWNELCHIAETMARGLAYLHEDIPGLK
daf-1       IGSDRVDTGFVTELWLVIEYHPSGSLHDFLLENTVNIETYYNLMRSTASGLAFLHNQIGGSK
subdomains                    V                                   VI-A cons.aa          DLK   N               DFG
hTGFBR-II   -GRPKMPIVHRDLKSSNILVKNDLTCCLCDFGLSLRL---GPYSSVDDLANSGQVGTARYMAP
mActR-IIB   GEGHKPSIAHRDFKSKNVLLKSDLTAVLADFGLAVRF----EPGKPPGD--THGQVGTRRYMAP
mActR-II    -DGHKPAISHRDIKSKNVLKNNLTACIADFGLALKF---EAGKSAGD--THGQVGTRRYMAP
daf-1       -ESNKPAMAHRDIKSKNIMYKNDLTCAIGDLGLSLSKPEDAASDIIAN--ENYKCGTVRYLAP
subdomains          VI-B                    VII                      VIII
```

FIG. 2A

```
a.a         C   C   E   G   N   M   C
5' GCGGATCCTGTTGTGAAGGNAATATGTG 3'
   BAMHI    C   C       G       C
```

FIG. 2B

```
a.a         V   A   V   K   I   F
5' GCGGATCCGTCGCAGTCAAAATTTT 3'
   BamHI        G   C   G   G   C
                T   T   T       A
```

FIG. 2C

```
a.a         R   D   I   K   S   K   N
5' GCGGATCCGCGATATTAAAAGCAA 3'
   BAMHI    A       C   C   GTCT
            G           A
```

FIG. 2D

```
a.a       E   P   A   M   Y
5' CGGAATTCTGGTGCCATATA
   EcoRI  G   G           G
          A   A
```

FIG. 3A

[Sequence alignment figure showing multiple protein sequences aligned. The sequences are labeled: ActR-II, ActR-IIB, TβR-II, TβR-I/ALK-5, ALK-1, ALK-2, ALK-3, ALK-4, ALK-6.]

```
                                                              ActR-II
                                                              ActR-IIB
                                                              TβR-II
                                                              TβR-I/ALK-5
                                                              ALK-1
                                                              ALK-2
                                                              ALK-3
                                                              ALK-4
                                                              ALK-6

DHDAEARLSAGCVGERITQMQRLTNIITTEDIVTVVTMVTNVDFP     ActR-II
DHDAEARLSAGCVEERVSLIRRSVNGTTSDCLVSLVTSVTNVDLL     ActR-IIB
DHDPEARLTAQCVAERFSELEHLDRLSGRSCSEEKIPEDGSLNTT     TβR-II
YANGAARLTALRIKKTLSQLSQQEGIKM(503)                 TβR-I/ALK-5
YPNPSARLTALRIKKTLQKHISNSPEKPKVIQ(503)             ALK-1
YQNPSARLTALRIKKTLTRKIDNSLDKLKTDC(509)             ALK-2
AHNPASRLTALRIKKTLAKMVESQDVKI(532)                 ALK-3
YANGAARLTALRIKKTLSQLSVQEDVKI(505)                 ALK-4
AQNPASRLTALRVKKTLAKMSESQDIKL(502)                 ALK-6

XI

PKESSL  (513)       ActR-II
PKESSI  (536)       ActR-IIB
K       (567)       TβR-II
```

FIG. 5

| Majority | |
|---|---|
| `C - F - - - - C - - - - - - - - - - - - - - - - - - - - - - - - - - - - - - - - - - - - - - - - - - - - - - - - - - - - - - - - - - - - - - - - - - - - - - - - - - - - - - - - - CXGD - DI - - TCET - - G - CFVSL - - SDG` | |

| Sequence | Label |
|---|---|
| `C - T - - - - CESP - - - - - - - - - - - - - - - - - - - - - - - - - - - - - - - - - - - - - - - - - - - - - - - - - - - - - - - - - - - - - - - - - - - - - - - - - - - - - - - - - - - - - - - - - - - HCKGP - - - TCR - - GAWCTVLVREEG` | AKL-1/CR |
| `C - - - - - - - - - - - - V - - - - - - - - - - - - - - - - - - - - - - - - - - - - - - - - - - - - - - - - - - - - - - - - - - - - - - - - - - - - - - - - - - - - - - - - - - - - - - - - - - - - - - - - - SCGNEDHCEGQQ - - CFSSLSINDG` | AKL-2/CR |
| `C - - Y - - - - CSG - - - - - - - CEGL - - - - - - - - - - - - - - - - - - - - - - - - - - - - - - - - - - - - - - - - - - - - - - - - - - - - - - - - - - - - - - - - - - - - - - - - - - - - - - - - - - HCPDD - AINNTCIT - NGHCFAIEEDDQ` | AKL-3/CR |
| `C - - A - - - - CTS - - - - - - - - - - - - - - - - - - - - - - - - - - - - - - - - - - - - - - - - - - - - - - - - - - - - - - - - - - - - - - - - - - - - - - - - - - - - - - - - - - - - - - - - - - CLQA - NY - - TCET - DGACMVSFFNLDG` | AKL-4/CR |
| `C - - F - - - - CHL - - - - - - - - - - - - - - - - - - - - - - - - - - - - - - - - - - - - - - - - - - - - - - - - - - - - - - - - - - - - - - - - - - - - - - - - - - - - - - - - - - - - - - - - - - - CTKD - NF - - TCVT - DGLCFVSVTETTD` | AKL-5/CR |
| `CLFFN - - - - - - - - - - - - ANWEKDRTNQTGVEPCYG - DKRRHCFAT - - - - WKNI - - SGS` | ActR-II/CR |
| `CIYYN - - - - - - - - - - - - ANWELERTNQSGLERCEGEQDKRLHCYAS - - - - WRNS - - SGT` | ActR-IIB/CR |
| `CKF - - - - CDVRFST - - - - - - - - CDNQKSCMSNCSITSIC - EKPQEVCAVWRKNDE` | TβR-II/CR |
| `CHCSREVGCNARTTGWVPGIEFLNETDRSFYENT - - - - CYTD - GSCYQSA - - RPS` | DAF-1/CR |

| Majority | |
|---|---|
| `IEIVEKGC - - - - - - - - - - - - - - - - - - CYDRTL - - - - - GSPF - CVKSPKSPG - TVTEC - CEGDLC` | |

| Sequence | Label |
|---|---|
| `RHPQEHRG - - - - - - - - - - - - - - - - - - - - - - - - - - - - - - - - - - - - - - - - - - - - - - - - - - - - - - - REL - CRGRPTE - - FVNHYC - - CDSHLC` | AKL-1/CR |
| `FHVYQKGC - - - - - - - - - - - - - - - - - - - - - - FQVY - - - - - - - - - - - - - - - - - - - - - - - - - - - EQGKMTC - - EC - - CQGDWC` | AKL-2/CR |
| `GETTLASG - - - - - - - - - - - - - - - - - - - - - - CMKYE - - - - - - - - - - - - - - - - - - - - - - - - GSDFQCKDSPKAQLRRTIEC - - CRTNLC` | AKL-3/CR |
| `MEHHVRTC - - - - - - - - - - - - - - - - - - - - - - - IPKVELVPAGKPFYCLSSED - - - LRNTHC - - CYTDYC` | AKL-4/CR |
| `KVIHNSMC - - - - - - - - - - - - - - - - - - - - - IAEIDLIPRDRPFVCAPSSKTGSVTTTYC - - CNQDHC` | AKL-5/CR |
| `IEIVKQGCWLDDINCYDRTD - - - - - - CVEKKDSPE - - - - VYFCCCEGNMC` | ActR-II/CR |
| `LELVKKGCWLDDFNCYDRQE - - - - - - CVATEENPQ - - - VYFCCCEGNFC` | ActR-IIB/CR |
| `NITLETVCHDPKLPYHDFILEDAASPKCIMKEKKKPGETFFMCSSDEC` | TβR-II/CR |
| `PEISHFGC - MDEKSVTDETEFHDTAAKVCTNNTKDPHATVWICCDKGNFC` | DAF-1/CR |

| ALK-2 | ALK-3 | ALK-4 | ALK-5 | ActR-II | ActR-IIB | TβR-II | daf-1 | |
|---|---|---|---|---|---|---|---|---|
| 79 | 60 | 61 | 63 | 40 | 40 | 37 | 39 | ALK-1 |
|  | 63 | 64 | 65 | 41 | 39 | 37 | 39 | ALK-2 |
|  |  | 63 | 65 | 41 | 38 | 37 | 39 | ALK-3 |
|  |  |  | 90 | 41 | 40 | 39 | 42 | ALK-4 |
|  |  |  |  | 42 | 40 | 41 | 43 | ALK-5 |
|  |  |  |  |  | 78 | 48 | 35 | ActR-II |
|  |  |  |  |  |  | 47 | 32 | ActR-IIB |
|  |  |  |  |  |  |  | 34 | TβR-II |

- ALK-3
- ALK-6
- TβR-I/ALK-5
- ALK-4
- ALK-1
- TβR-I/Tsk-7L/ALK-2/SKR1
- ActR-II
- ActR-IIB
- TβR-II
- Daf-1

FIG. 8
| FLAG-Smad5 | - | + | + | + |
|---|---|---|---|---|
| c.a. ALK1-HA | - | - | + | - |
| c.a. ALK5-HA | - | - | - | + |
IP : anti-FLAG
Blot : anti-phosphoserine
IP : anti-FLAG
Blot : anti-FLAG
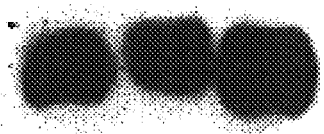
IP : (-)
Blot : anti-HA
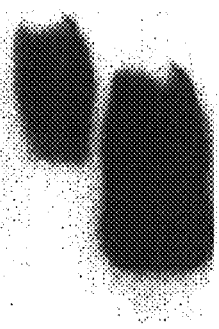

PROTEINS HAVING SERINE/THREONINE KINASE DOMAINS, CORRESPONDING NUCLEIC ACID MOLECULES, AND THEIR USE

This application is a continuation-in-part of application Ser. No. 09/039,177 filed Mar. 3, 1998 which is a continuation-in-part of application Ser. No. 08/436,265 filed Oct. 30, 1995, now U.S. Pat. No. 6,316,217, which is a National Stage of PCT/GB93/02367 filed Nov. 17, 1993.

FIELD OF THE INVENTION

This invention relates to proteins having serine/threonine kinase domains, corresponding nucleic acid molecules, and their use.

BACKGROUND OF THE INVENTION

The transforming growth factor-β (TGF-β) superfamily consists of a family of structurally-related proteins, including three different mammalian isoforms of TGF-β (TGF-β1, β2 and β3), activins, inhibins, müllerian-inhibiting substance and bone morphogenic proteins (BMPs) (for reviews see Roberts and Sporn, (1990) Peptide Growth Factors and Their Receptors, Pt.1, Sporn and Roberts, eds. (Berlin: Springer-Verlag) pp 419–472; Moses et al (1990) Cell 63, 245–247). The proteins of the TGF-β superfamily have a wide variety of biological activities. TGF-β acts as a growth inhibitor for many cell types and appears to play a central role in the regulation of embryonic development, tissue regeneration, immuno-regulation, as well as in fibrosis and carcinogenesis (Roberts and Sporn (199) see above).

Activins and inhibins were originally identified as factors which regulate secretion of follicle-stimulating hormone secretion (Vale et al (1990) Peptide Growth Factors and Their Receptors, Pt.2, Sporn and Roberts, eds. (Berlin: Springer-Verlag) pp.211–248). Activins were also shown to induce the differentiation of haematopoietic progenitor cells (Murata et al (1988) Proc. Natl. Acad. Sci. USA 85, 2434–2438; Eto et al (1987) Biochem. Biophys. Res. Commun. 142, 1095–1103) and induce mesoderm formation in Xenopus embryos (Smith et al (1990) Nature 345, 729–731; van den Eijnden-Van Raaij et al (1990) Nature 345, 732–734).

BMPs or osteogenic proteins which induce the formation of bone and cartilage when implanted subcutaneously (Wozney et al (1988) Science 242, 1528–1534), facilitate neuronal differentiation (Paralkar et al (1992) J. Cell Biol. 119, 1721–1728) and induce monocyte chemotaxis (Cunningham et al (1992) Proc. Natl. Acad. Sci. USA 89, 11740–11744). Müllerian-inhibiting substance induces regression of the Müllerian duct in the male reproductive system (Cate et al (1986) Cell 45, 685–698), and a glial cell line-derived neurotrophic factor enhances survival of midbrain dopaminergic neurons (Lin et al (1993) Science 260, 1130–1132). The action of these growth factors is mediated through binding to specific cell surface receptors.

Within this family, TGF-β receptors have been most thoroughly characterized. By covalently cross-linking radio-labelled TGF-β to cell surface molecules followed by polyacrylamide gel electrophoresis of the affinity-labelled complexes, three distinct size classes of cell surface proteins (in most cases) have been identified, denoted receptor type I (53 kd), type II (75 kd), type III or betaglycan (a 300 kd proteoglycan with a 120 kd core protein) (for a review see Massague (1992) Cell 69 1067–1070) and more recently endoglin (a homodimer of two 95 kd subunits) (Cheifetz et al (1992) J. Biol. Chem. 267 19027–19030). Current evidence suggests that type I and type II receptors are directly involved in receptor signal transduction (Segarini et al (1989) Mol. Endo., 3, 261–272; Laiho et al (1991) J. Biol. Chem. 266, 9100–9112) and may form a heteromeric complex; the type II receptor is needed for the binding of TGF-β to the type I receptor and the type I receptor is needed for the signal transduction induced by the type II receptor (Wrana et al (1992) Cell, 71, 1003–1004). The type III receptor and endoglin may have more indirect roles, possibly by facilitating the binding of ligand to type II receptors (Wang et al (1991) Cell, 67 797–805; López-Casillas et al (1993) Cell, 73 1435–1444).

Binding analyses with activin A and BMP4 have led to the identification of two co-existing cross-linked affinity complexes of 50–60 kDa and 70–80 kDa on responsive cells (Hino et al (1989) J. Biol. Chem. 264, 10309–10314; Mathews and Vale (1991), Cell 68, 775–785; Paralker et al (1991) Proc. Natl. Acad. Sci. USA 87, 8913–8917). By analogy with TGF-β receptors they are thought to be signalling receptors and have been named type I and type II receptors.

Among the type II receptors for the TGF-β superfamily of proteins, the cDNA for the activin type II receptor (Act RII) was the first to be cloned (Mathews and Vale (1991) Cell 65, 973–982). The predicted structure of the receptor was shown to be a transmembrane protein with an intracellular serine/threonine kinase domain. The activin receptor is related to the C. elegans daf-1 gene product, but the ligand is currently unknown (Georgi et al (1990) Cell 61, 635–645). Thereafter, another form of the activin type II receptor (activin type IIB receptor), of which there are different splicing variants (Mathews et al (1992), Science 225, 1702–1705; Attisano et al (1992) Cell 68, 97–108), and the TGF-β type II receptor (TβRII) (Lin et al (1992) Cell 68, 775–785) were cloned, both of which have putative serine/threonine kinase domains.

SUMMARY OF THE INVENTION

The present invention involves the discovery of related novel peptides, including peptides having the activity of those defined herein as SEQ ID Nos. 2, 4, 8, 10, 12, 14, 16 and 18. Their discovery is based on the realisation that receptor serine/threonine kinases form a new receptor family, which may include the type II receptors for other proteins in the TGF-β superfamily. To ascertain whether there were other members of this family of receptors, a protocol was designed to clone ActRII/daf I related cDNAs. This approach made use of the polymerase chain reaction (PCR), using degenerate primers based upon the amino-acid sequence similarity between kinase domains of the mouse activin type II receptor and daf-I gene products.

This strategy resulted in the isolation of a new family of receptor kinases called Activin receptor like kinases (ALK's) 1–6. These cDNAs showed an overall 33–39% sequence similarity with ActRII and TGF-β type II receptor and 40–92% sequence similarity towards each other in the kinase domains.

Soluble receptors according to the invention comprise at least predominantly the extracellular domain. These can be selected from the information provided herein, prepared in conventional manner, and used in any manner associated with the invention.

Antibodies to the peptides described herein may be raised in conventional manner. By selecting unique sequences of the peptides, antibodies having desired specificity can be obtained.

The antibodies may be monoclonal, prepared in known manner. In particular, monoclonal antibodies to the extracellular domain are of potential value in therapy.

Products of the invention are useful in diagnostic methods, e.g. to determine the presence in a sample for an analyte binding therewith, such as in an antagonist assay. Conventional techniques, e.g. an enzyme-linked immunosorbent assay, may be used.

Products of the invention having a specific receptor activity can be used in therapy, e.g. to modulate conditions associated with activin or TGF-β activity. Such conditions include fibrosis, e.g. liver cirrhosis and pulmonary fibrosis, cancer, rheumatoid arthritis and glomeronephritis.

BRIEF DESCRIPTION OF THE DRAWINGS

FIG. 1 shows the alignment of the serine/threonine (S/T) kinase domains (I–VIII) of related receptors from transmembrane proteins, including embodiments of the present invention. The nomenclature of the subdomains is accordingly to Hanks et al (1988). The sequences displayed are (from top to bottom) SEQ ID NO: 30 to 33.

FIGS. 2A to 2D shows the sequences and characteristics of the respective primers used in the initial PCR reactions. The nucleic acid sequences are also given as SEQ ID Nos. 19 to 22.

FIG. 5 shows the sequence alignment of the cysteine-rich domains of the ALKs (position 34–95 of SEQ ID NO: 2, position 35–99 of SEQ ID NO: 4, position 59–130 of SEQ ID NO: 6, position 34–101 of SEQ ID NO: 8 and position 34–106 of SEQ ID No: 9), TβR-II (position 30–110 of SEQ ID NO: 36), Act R-II (position 29–109 of SEQ ID NO: 34), Act R-IIB (position 49–143 of SEQ ID NO: 35) and daf-1 (position 56–152 of SEQ ID NO: 37) receptors.

FIG. 8 depicts the phosphorylation of Smad-5 following interaction with ALK-1 but not following interaction with ALK-5.

BRIEF DESCRIPTION OF THE SEQUENCE LISTINGS

Figure 3B:
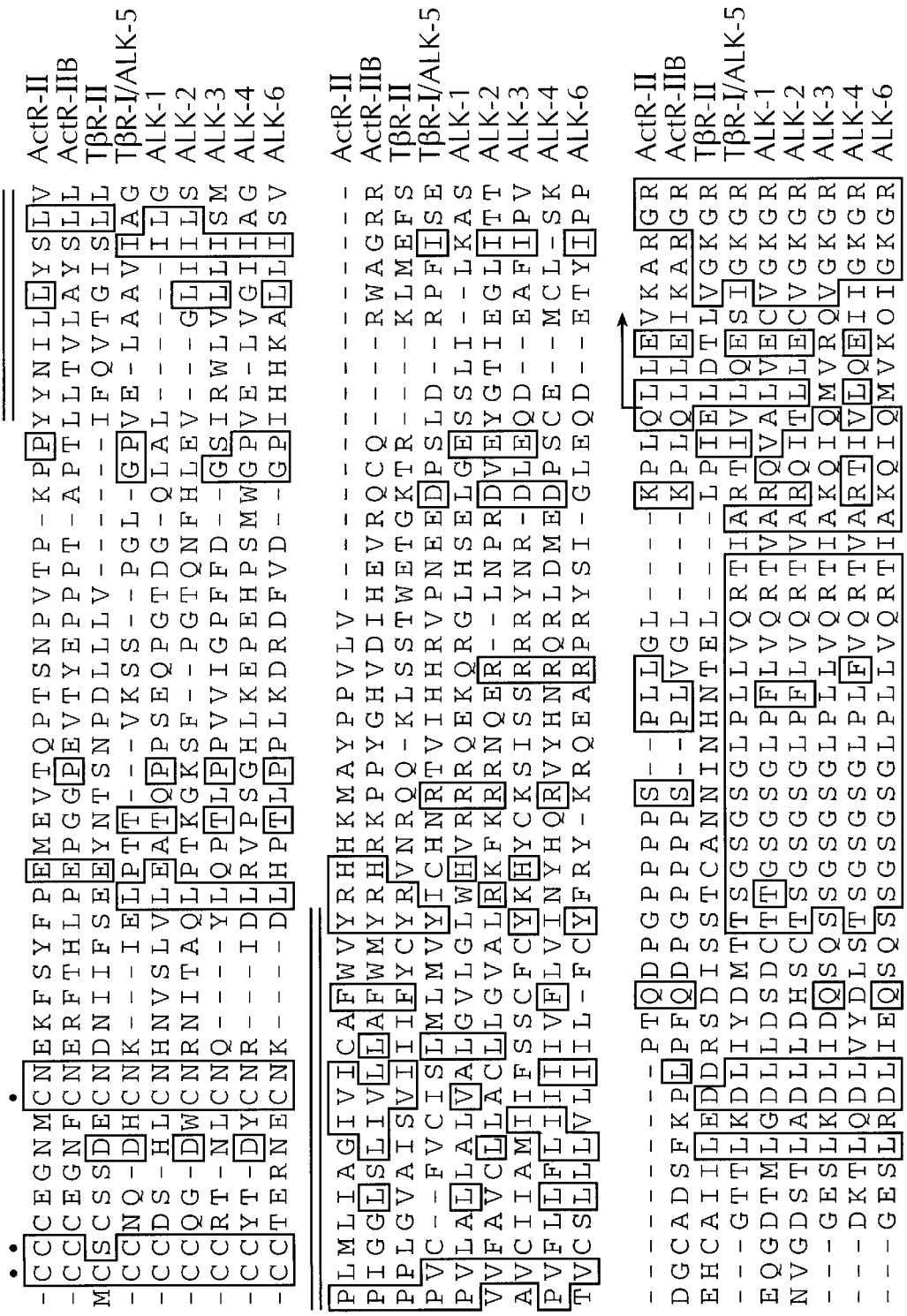
FIG. 3 is a comparison of the amino-acid sequences of human activin type II receptor (Act R-II)(SEQ ID NO: 34), mouse activin type IIB receptor (Act R-IIB)(SEQ ID NO: 35), human TGF-β type II receptor (TβR-II)(SEQ ID NO: 36), human TGF-β type I receptor (ALK-5)(SEQ ID NO: 10), human activin receptor type IA (ALK-2)(SEQ ID NO:4), and type IB (ALK-4)(SEQ ID NO: 8), ALKs 1 & 3 (SEQ ID NO: 2 and SEQ ID NO: 6) and mouse ALK-6 (SEQ ID NO: 18).

Sequences 1 and 2 are the nucleotide and deduced amino-acid sequences of cDNA for hALK-1 (clone HP57).

Sequences 3 and 4 are the nucleotide and deduced amino-acid sequences of cDNA for hALK-2 (clone HP53).

Sequences 5 and 6 are the nucleotide and deduced amino-acid sequences of cDNA for hALK-3 (clone ONF5).

Sequences 7 and 8 the nucleotide and deduced amino-acid sequences of cDNA for hALK-4 (clone 11H8), complemented with PCR product encoding extracellular domain.

Sequences 9 and 10 are the nucleotide and deduced amino-acid sequences of cDNA for hALK-5 (clone EMBLA).

Sequences 11 and 12 are the nucleotide and deduced amino-acid sequences of cDNA for mALK-1 (clone AM6).

Sequences 13 and 14 are the nucleotide and deduced amino-acid sequences of cDNA for mALK-3 (clones ME-7 and ME-D).

Sequences 15 and 16 are the nucleotide and deduced amino-acid sequences of cDNA for mALK-4 (clone 8a1).

Sequences 17 and 18 are the nucleotide and deduced amino-acid sequences of cDNA for mALK-6 (clone ME-6).

Sequence 19 (B1-S) is a sense primer, extracellular domain, cysteine-rich region, BamHI site at 5' end, 28-mer, 64-fold degeneracy.

Sequence 20 (B3-S) is a sense primer, kinase domain II, BamHI site at 5' end, 25-mer, 162-fold degeneracy.

Sequence 21 (B7-S) is a sense primer, kinase domain VIB, S/T kinase specific residues, BamHI site at 5' end, 24-mer, 288-fold degeneracy.

Sequence 22 (E8-AS) is an anti-sense primer, kinase domain, S/T kinase-specific residues EcoRI site at 5' end, 20-mer, 18-fold degeneracy.

Sequence 23 is an oligonucleotide probe.

Sequence 24 is a 5' primer.

Sequence 25 is a 3' primer.

Sequence 26 is a consensus sequence in Subdomain I.

Sequences 27 and 28 are novel sequence motifs in Subdomain VIB.

Sequence 29 is a novel sequence motif in Subdomain VIII.

DESCRIPTION OF THE INVENTION

As described in more detail below, nucleic acid sequences have been isolated, coding for a new sub-family of serine/threonine receptor kinases. The term nucleic acid molecules as used herein refers to any sequence which codes for the murine, human or mammalian form, amino-acid sequences of which are presented herein. It is understood that the well known phenomenon of codon degeneracy provides for a great deal of sequence variation and all such varieties are included within the scope of this invention.

The nucleic acid sequences described herein may be used to clone the respective genomic DNA sequences in order to study the genes' structure and regulation. The murine and human cDNA or genomic sequences can also be used to isolate the homologous genes from other mammalian species. The mammalian DNA sequences can be used to study the receptors' functions in various in vitro and in vivo model systems.

As exemplified below for ALK-5 cDNA, it is also recognised that, given the sequence information provided herein, the artisan could easily combine the molecules with a pertinent promoter in a vector, so as to produce a cloning vehicle for expression of the molecule. The promoter and coding molecule must be operably linked via any of the well-recognized and easily-practised methodologies for so doing. The resulting vectors, as well as the isolated nucleic acid molecules themselves, may be used to transform prokaryotic cells (e.g. *E. coli*), or transfect eukaryotes such as yeast (*S. cerevisiae*), PAE, COS or CHO cell lines. Other appropriate expression systems will also be apparent to the skilled artisan.

Several methods may be used to isolate the ligands for the ALKs. As shown for ALK-5 cDNA, cDNA clones encoding the active open reading frames can be subcloned into expression vectors and transfected into eukaryotic cells, for example COS cells. The transfected cells which can express the receptor can be subjected to binding assays for radioactively-labelled members of the TGF-β superfamily (TGF-β, activins, inhibins, bone morphogenic proteins and mullerian-inhibiting substances), as it may be expected that the receptors will bind members of the TGF-β superfamily. Various biochemical or cell-based assays can be designed to identify the ligands, in tissue extracts or conditioned media, for receptors in which a ligand is not, known. Antibodies raised to the receptors may also be used to identify the ligands, using the immunoprecipitation of the cross-linked complexes. Alternatively, purified receptor could be used to isolate the ligands using an affinity-based approach. The determination of the expression patterns of the receptors may also aid in the isolation of the ligand. These studies may be carried out using ALK DNA or RNA sequences as probes to perform in situ hybridisation studies.

The use of various model systems or structural studies should enable the rational development of specific agonists and antagonists useful in regulating receptor function. It may be envisaged that these can be peptides, mutated ligands, antibodies or other molecules able to interact with the receptors.

The foregoing provides examples of the invention Applicants intend to claim which includes, inter alia, isolated nucleic acid molecules coding for activin receptor-like kinases (ALKs), as defined herein. These include such sequences isolated from mammalian species such as mouse, human, rat, rabbit and monkey.

The following description relates to specific embodiments. It will be understood that the specification and examples are illustrative but not limitative of the present invention and that other embodiments within the spirit and scope of the invention will suggest themselves to those skilled in the art.

Preparation of mRNA and Construction of a cDNA Library

For construction of a cDNA library, poly (A)$^+$ RNA was isolated from a human erythroleukemia cell line (HEL 92.1.7) obtained from the American Type Culture Collection (ATCC TIB 180). These cells were chosen as they have been shown to respond to both activin and TGF-β. Moreover leukaemic cells have proved to be rich sources for the cloning of novel receptor tyrosine kinases (Partanen et al (1990) Proc. Natl. Acad. Sci. USA 87, 8913–8917 and (1992) Mol. Cell. Biol. 12, 1698–1707). (Total) RNA was prepared by the guanidinium isothiocyanate method (Chirgwin et al (1979) Biochemistry 18, 5294–5299). mRNA was selected using the poly-A or poly AT tract mRNA isolation kit (Promega, Madison, Wis., U.S.A.) as described by the manufacturers, or purified through an oligo (dT)-cellulose column as described by Aviv and Leder (1972) Proc. Natl. Acad. Sci. USA 69, 1408–1412. The isolated mRNA was used for the synthesis of random primed (Amersham) cDNA, that was used to make a λgt10 library with 1×10$^5$ independent cDNA clones using the Riboclone cDNA synthesis system (Promega) and λgt10 in vitro packaging kit (Amersham) according to the manufacturers' procedures. An amplified oligo (dT) primed human placenta λZAPII cDNA library of 5×10$^5$ independent clones was used. Poly (A)$^+$ RNA isolated from AG1518 human foreskin fibroblasts was used to prepare a primary random primed λZAPII cDNA library of 1.5×10$^6$ independent clones using the RiboClone cDNA synthesis system and Gigapack Gold II packaging extract (Stratagene). In addition, a primary oligo (dT) primed human foreskin fibroblast λgt10 cDNA library (Claesson-Welsh et al (1989) Proc. Natl. Acad. Sci. USA. 86 4917–4912) was prepared. An amplified oligo (dT) primed HEL cell λgt11 cDNA library of 1.5×10$^6$ independent clones (Poncz et al (1987) Blood 69 219–223) was used. A twelve-day mouse embryo λEXIox cDNA library was obtained from Novagen (Madison, Wis., U.S.A.); a mouse placenta λZAPII cDNA library was also used.

Generation of cDNA Probes by PCR

For the generation of cDNA probes by PCR (Lee et al (1988) Science 239, 1288–1291) degenerate PCR primers were constructed based upon the amino-acid sequence similarity between the mouse activin type II receptor (Mathews and Vale (1991) Cell 65, 973–982) and daf-1 (George et al (1990) Cell 61, 635–645) in the kinase domains II and VIII. FIG. 1 shows the aligned serine/threonine kinase domains (I–VIII), of four related receptors of the TGF-β superfamily, i.e. hTβR-II, mActR-IIB, mActR-II and the daf-1 gene product, using the nomenclature of the subdomains according to Hanks et al (1988) Science 241, 45–52.

Several considerations were applied in the design of the PCR primers. The sequences were taken from regions of homology between the activin type II receptor and the daf-1 gene product, with particular emphasis on residues that confer serine/threonine specificity (see Table 2) and on residues that are shared by transmembrane kinase proteins and not by cytoplasmic kinases. The primers were designed so that each primer of a PCR set had an approximately similar GC composition, and so that self complementarity and complementarity between the 3' ends of the primer sets were avoided. Degeneracy of the primers was kept as low as possible, in particular avoiding serine, leucine and arginine residues (6 possible codons), and human codon preference was applied. Degeneracy was particularly avoided at the 3' end as, unlike the 5' end, where mismatches are tolerated, mismatches at the 3' end dramatically reduce the efficiency of PCR.

In order to facilitate directional subcloning, restriction enzyme sites were included at the 5' end of the primers, with a GC clamp, which permits efficient restriction enzyme digestion. The primers utilised are shown in FIG. 2. Oligonucleotides were synthesized using Gene assembler plus (Pharmacia-LKB) according to the manufacturers instructions.

The mRNA prepared from HEL cells as described above was reverse-transcribed into cDNA in the presence of 50 mM Tris-HCl, pH 8.3, 8 mM MgCl$_2$, 30 mM KCl, 10 mM dithiothreitol, 2 mM nucleotide triphosphates, excess oligo (dT) primers and 34 units of AMV reverse transcriptase at 42° C. for 2 hours in 40 μl of reaction volume. Amplification by PCR was carried out with a 7.5% aliquot (3 μl) of the reverse-transcribed mRNA, in the presence of 10 mM Tris-HCl, pH 8.3, 50 mM KCl, 1.5 M MgCl$_2$, 0.01% gelatin, 0.2 mM nucleotide triphosphates, 1 μM of both sense and antisense primers and 2.5 units of Taq polymerase (Perkin Elmer Cetus) in 100 μl reaction volume. Amplifications were performed on a thermal cycler (Perkin Elmer Cetus) using the following program: first 5 thermal cycles with denaturation for 1 minute at 94° C., annealing for 1 minute at 50° C., a 2 minute ramp to 55° C. and elongation for 1 minute at 72° C., followed by 20 cycles of 1 minute at 94° C., 30 seconds at 55° C. and 1 minute at 72° C. A second round of PCR was performed with 3 μl of the first reaction as a template. This involved 25 thermal cycles, each composed of 94° C. (1 min), 55° C. (0.5 min), 72° C. (1 min).

General procedures such as purification of nucleic acids, restriction enzyme digestion, gel electrophoresis, transfer of nucleic acid to solid supports and subcloning were performed essentially according to established procedures as described by Sambrook et al, (1989), Molecular cloning: A Laboratory Manual, $2^{nd}$ Ed. Cold Spring Harbor Laboratory (Cold Spring Harbor, N.Y., USA).

Samples of the PCR products were digested with BamHI and EcoRI and subsequently fractionated by low melting point agarose gel electrophoresis. Bands corresponding to the approximate expected sizes, (see Table 1: ≈460 bp for primer pair B3-S and E8-AS and ≈140 bp for primer pair B7-S and E8-AS) were excised from the gel and the DNA was purified. Subsequently, these fragments were ligated into pUC19 (Yanisch-Perron et al (1985) Gene 33, 103–119), which had been previously linearised with BamHI and EcoR1 and transformed into E. coli strain DH5α using standard protocols (Sambrook et al, supra). Individual clones were sequenced using standard double-stranded sequencing techniques and the dideoxynucleotide chain termination method as described by Sanger et al (1977) Proc. Natl. Acad. Sci. USA 74, 5463–5467, and T7 DNA polymerase.

Employing Reverse Transcriptase PCR on HEL mRNA with the primer pair B3-S and E8-AS, three PCR products were obtained, termed 11.1, 11.2 and 11.3, that corresponded to novel genes. Using the primer pair B7-S and E8-AS, an additional novel PCR product was obtained termed 5.2.

TABLE 1

| NAME OF PCR PRODUCT | PRIMERS | INSERT SIZE (bp) | SIZE OF DNA FRAGMENT IN mActRII/ hTβRII CLONES (bp) | SEQUENCE IDENTITY WITH SEQUENCE mActRII/ hTβRII (%) | SEQUENCE IDENTITY BETWEEN mActRII and TβR-II (%) |
|---|---|---|---|---|---|
| 11.1 | B3-S/E8-AS | 460 | 460 | 46/40 | 42 |
| 11.2 | B3-S/E8-AS | 460 | 460 | 49/44 | 47 |
| 11.3 | B3-S/E8-AS | 460 | 460 | 44/36 | 48 |
| 11.29 | B3-S/E8-AS | 460 | 460 | ND/100 | ND |
| 9.2 | B1-S/E8-AS | 800 | 795 | 100/ND | ND |
| 5.2 | B7-S/E8-AS | 140 | 143 | 40/38 | 60 |

Isolation of cDNA Clones

The PCR products obtained were used to screen various cDNA libraries described supra. Labelling of the inserts of PCR products was performed using random priming method (Feinberg and Vogelstein (1983) Anal. Biochem, 132 6–13) using the Megaprime DNA labelling system (Amersham). The oligonucleotide derived from the sequence of the PCR product 5.2 was labelled by phosphorylation with T4 polynucleotide kinase following standard protocols (Sambrook et al, supra). Hybridization and purification of positive bacteriophages were performed using standard molecular biological techniques.

The double-stranded DNA clones were all sequenced using the dideoxynucleotide chain-termination method as described by Sanger et al, supra, using T7 DNA polymerase (Pharmacia-LKB) or Sequenase (U.S. Biochemical Corporation, Cleveland, Ohio, U.S.A.). Compressions of nucleotides were resolved using 7-deaza-GTP (U.S. Biochemical Corp.) DNA sequences were analyzed using the DNA STAR computer program (DNA STAR Ltd. U.K.).

Analyses of the sequences obtained revealed the existence of six distinct putative receptor serine/threonine kinases which have been named ALK 1–6.

To clone cDNA for ALK-1 the oligo (dT) primed human placenta cDNA library was screened with a radiolabelled insert derived from the PCR product 11.3; based upon their restriction enzyme digestion patterns, three different types of clones with approximate insert sizes of 1.7. kb, 2 kb & 3.5 kb were identified. The 2 kb clone, named HP57, was chosen as representative of this class and subjected to complete sequencing. Sequence analysis of ALK-1 revealed a sequence of 1984 nucleotides including a poly-A tail (SEQ ID No. 1). The longest open reading frame encodes a protein of 503 amino-acids SEQ ID NO: 2, with high sequence similarity to receptor serine/threonine kinases (see below). The first methionine codon, the putative translation start site, is at nucleotide 283–285 and is preceded by an in-frame stop codon. This first ATG is in a more favourable context for translation initiation (Kozak (1987) Nucl. Acids Res., 15, 8125–8148) than the second and third in-frame ATG at nucleotides 316–318 and 325–327. The putative initiation codon is preceded by a 5' untranslated sequence of 282 nucleotides that is GC-rich (80% GC), which is not uncommon for growth factor receptors (Kozak (1991) J. Cell Biol., 115, 887–903). The 3' untranslated sequence comprises 193 nucleotides and ends with a poly-A tail. No bona fide poly-A addition signal is found, but there is a sequence (AATACA), 17–22 nucleotides upstream of the poly-A tail, which may serve as a poly-A addition signal.

ALK-2 cDNA was cloned by screening an amplified oligo (dT) primed human placenta cDNA library with a radiolabelled insert derived from the PCR product 11.2. Two clones, termed HP53 and HP64, with insert sizes of 2.7 kb and 2.4 kb respectively, were identified and their sequences were determined. No sequence difference in the overlapping clones was found, suggesting they are both derived from transcripts of the same gene.

Sequence analysis of cDNA clone HP53 (SEQ ID No. 3) revealed a sequence of 2719 nucleotides with a poly-A tail. The longest open reading frame encodes a protein of 509 amino-acids SEQ ID NO:4. The first ATG at nucleotides 104–106 agrees favourably with Kozak's consensus sequence with an A at position 3. This ATG is preceded in-frame by a stop codon. There are four ATG codons in close proximity further downstream, which agree with the Kozak's consensus sequence (Kozak, supra), but according to Kozak's scanning model the first ATG is predicted to be the translation start site. The 5' untranslated sequence is 103 nucleotides. The 3' untranslated sequence of 1089 nucleotides contains a polyadenylation signal located 9–14 nucleotides upstream from the poly-A tail. The cDNA clone HP64 lacks 498 nucleotides from the 5' end compared to HP53, but the sequence extended at the 3' end with 190 nucleotides and poly-A tail is absent. This suggests that different polyadenylation sites occur for ALK-2. In Northern blots, however, only one transcript was detected (see below).

The cDNA for human ALK-3 was cloned by initially screening an oligo (dT) primed human foreskin fibroblast cDNA library with an oligonucleotide (SEQ ID No. 23) derived from the PCR product 5.2. One positive cDNA clone with an insert size of 3 kb, termed ON11, was identified. However, upon partial sequencing, it appeared that this clone was incomplete; it encodes only part of the kinase domain and lacks the extracelluar domain. The most 5' sequence of ON11, a 540 nucleotide XbaI restriction fragment encoding a truncated kinase domain, was subsequently used to probe a random primed fibroblast cDNA library from which one cDNA clone with an insert size of 3 kb, termed ONF5, was isolated (SEQ ID No. 5). Sequence analysis of ONF5 revealed a sequence of 2932 nucleotides without a poly-A tail, suggesting that this clone was derived by internal priming. The longest open reading frame codes for a protein of 532 amino-acids SEQ ID NO: 6. The first ATG codon which is compatible with Kozak's consensus sequence (Kozak, supra), is at 310–312 nucleotides and is preceded by an in-frame stop codon. The 5' and 3' untranslated sequences are 309 and 1027 nucleotides long, respectively.

ALK-4 cDNA was identified by screening a human oligo (dT) primed human erythroleukemia cDNA library with the radiolabelled insert of the PCR product 11.1 as a probe. One cDNA clone, termed 11H8, was identified with an insert size of 2 kb (SEQ ID No. 7). An open reading frame was found encoding a protein sequence of 383 amino-acids SEQ ID NO:8 encoding a truncated extracellular domain with high similarity to receptor serine/threonine kinases. The 3' untranslated sequence is 818 nucleotides and does not contain a poly-A tail, suggesting that the cDNA was internally primed. cDNA encoding the complete extracellular domain (nucleotides 1–366) was obtained from HEL cells by RT-PCR with 5' primer (SEQ ID No. 24) derived in part from sequence at translation start site of SKR-2 (a cDNA sequence deposited in GenBank data base, accesion number L10125, that is identical in part to ALK-4) and 3' primer (SEQ ID No. 25) derived from 11H8 cDNA clone.

ALK-5 was identified by screening the random primed HEL cell λgt 10 cDNA library with the PCR product 11.1 as a probe. This yielded one positive clone termed EMBLA (insert size of 5.3 kb with 2 internal EcoRI sites). Nucleotide sequencing revealed an open reading frame of 1509 bp, coding for 503 amino-acids. The open reading frame was flanked by a 5' untranslated sequence of 76 bp, and a 3' untranslated sequence of 3.7 kb which was not completely sequenced. The nucleotide and deduced amino-acid sequences of ALK-5 are shown in SEQ ID Nos. 9 (nucleotide sequence) and 10 (amino acid sequences). In the 5' part of the open reading frame, only one ATG codon was found; this codon fulfils the rules of translation initiation (Kozak, supra). An in-frame stop codon was found at nucleotides (−54)–(−52) in the 5' untranslated region. The predicted ATG start codon is followed by a stretch of hydrophobic amino-acid residues which has characteristics of a cleavable signal sequence. Therefore, the first ATG codon is likely to be used as a translation initiation site. A preferred cleavage site for the signal peptidase, according to von Heijne (1986) Nucl. Acid. Res. 14, 4683–4690, is located between amino-acid residues 24 and 25. The calculated molecular mass of the primary translated product of the ALK-5 without signal sequence is 53,646 Da.

Screening of the mouse embryo λEX Iox cDNA library using PCR, product 11.1 as a probe yielded 20 positive clones. DNAs from the positive clones obtained from this library were digested with EcoRI and HindIII, electrophoretically separated on a 1.3% agarose gel and transferred to nitrocellulose filters according to established procedures as described by Sambrook et al, supra. The filters were then hybridized with specific probes for human ALK-1 (nucleotide 288–670), ALK-2 (nucleotide 1–581), ALK-3 (nucleotide 79–824) or ALK-4 nucleotide 1178–1967). Such analyses revealed that a clone termed ME-7 hybridised with the human ALK-3 probe. However, nucleotide sequencing revealed that this clone was incomplete, and lacked the 5' part of the translated region. Screening the same cDNA library with a probe corresponding to the extracelluar domain of human ALK-3 (nucleotides 79–824) revealed the clone ME-D. This clone was isolated and the sequence was analyzed. Although this clone was incomplete in the 3' end of the translated region, ME-7 and ME-D overlapped and together covered the complete sequence of mouse ALK-3. The predicted amino-acid sequence of mouse ALK-3 is very similar to the human sequence; only 8 amino-acid residues differ (98% identity; see SEQ ID No. 14) and the calculated molecular mass of the primary translated product without the putative signal sequence is 57,447 Da.

Of the clones obtained from the initial library screening with PCR product 11.1, four clones hybridized to the probe corresponding to the conserved kinase domain of ALK-4 but not to probes from more divergent parts of ALK-1 to -4. Analysis of these clones revealed that they have an identical sequence which differs from those of ALK-1 to -5 and was termed ALK-6. The longest clone ME6 with a 2.0 kb insert was completely sequenced yielding a 1952 bp fragment consisting of an open reading frame of 1506 bp (502 amino-acids), flanked by a 5' untranslated sequence of 186 bp, and a 3' untranslated sequence of 160 bp. The nucleotide and predicted amino-acid sequences of mouse ALK-6 are shown in SEQ ID Nos. 17 and 18. No polyadenylation signal was found in the 3' untranslated region of ME6, indicating that the cDNA was internally primed in the 3' end. Only one ATG codon was found in the 5' part of the open reading frame, which fulfils the rules for translation initiation (Kozak, supra), and was preceded by an in-frame stop codon at nucleotides 163–165. However, a typical hydrophobic leader sequence was not observed at the N terminus of the translated region. Since there is no ATG codon and putative hydrophobic leader sequence, this ATG codon is likely to be used as a translation initiation site. The calculated molecular mass of the primary translated product with the putative signal sequence is 55,576 Da.

Mouse ALK-1 (clone AM6 with 1.9. kb insert) was obtained from the mouse placenta λZAPII cDNA library using human ALK-1 cDNA as a probe (see SEQ ID No. 11). Mouse ALK-4 (clone 8a1 with 2.3 kb insert) was also obtained from this library using human ALK-4 cDNA library as a probe (SEQ ID No. 15).

To summarise, clones HP22, HP57, ONF1, ONF3, ONF4 and HP29 encode the same gene, ALK-1. Clone AM6 encodes mouse ALK-1. HP53, HP64 and HP84 encode the same gene, ALK-2. ONF5, ONF2 and ON11 encode the same gene ALK-3. ME-7 and ME-D encode the mouse counterpart of human ALK-3. 11H8 encodes a different gene ALK-4, whilst 8a1 encodes the mouse equivalent. EMBLA encodes ALK-5, and ME-6 encodes ALK-6.

Figure 3C:
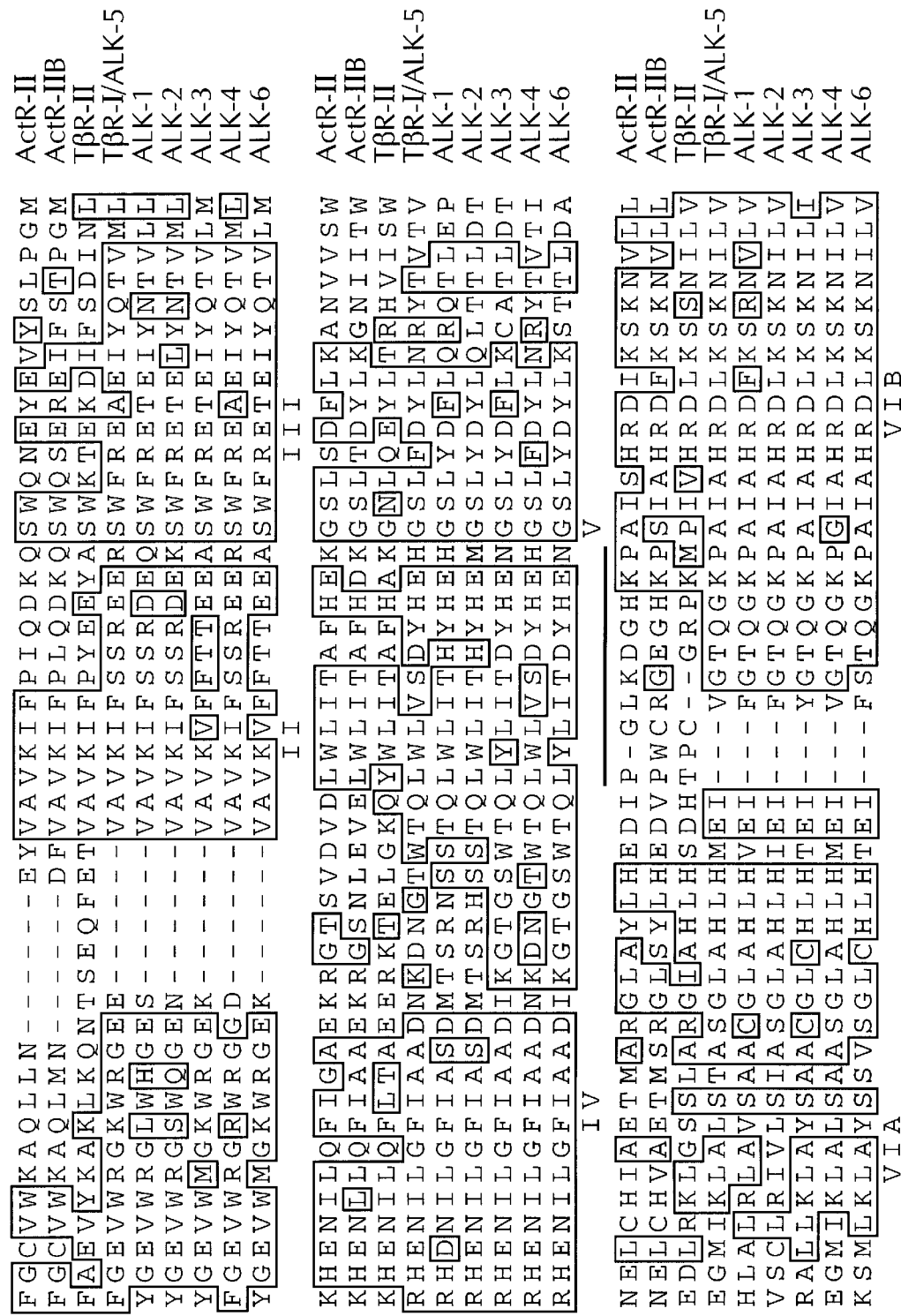
Figure 3D:
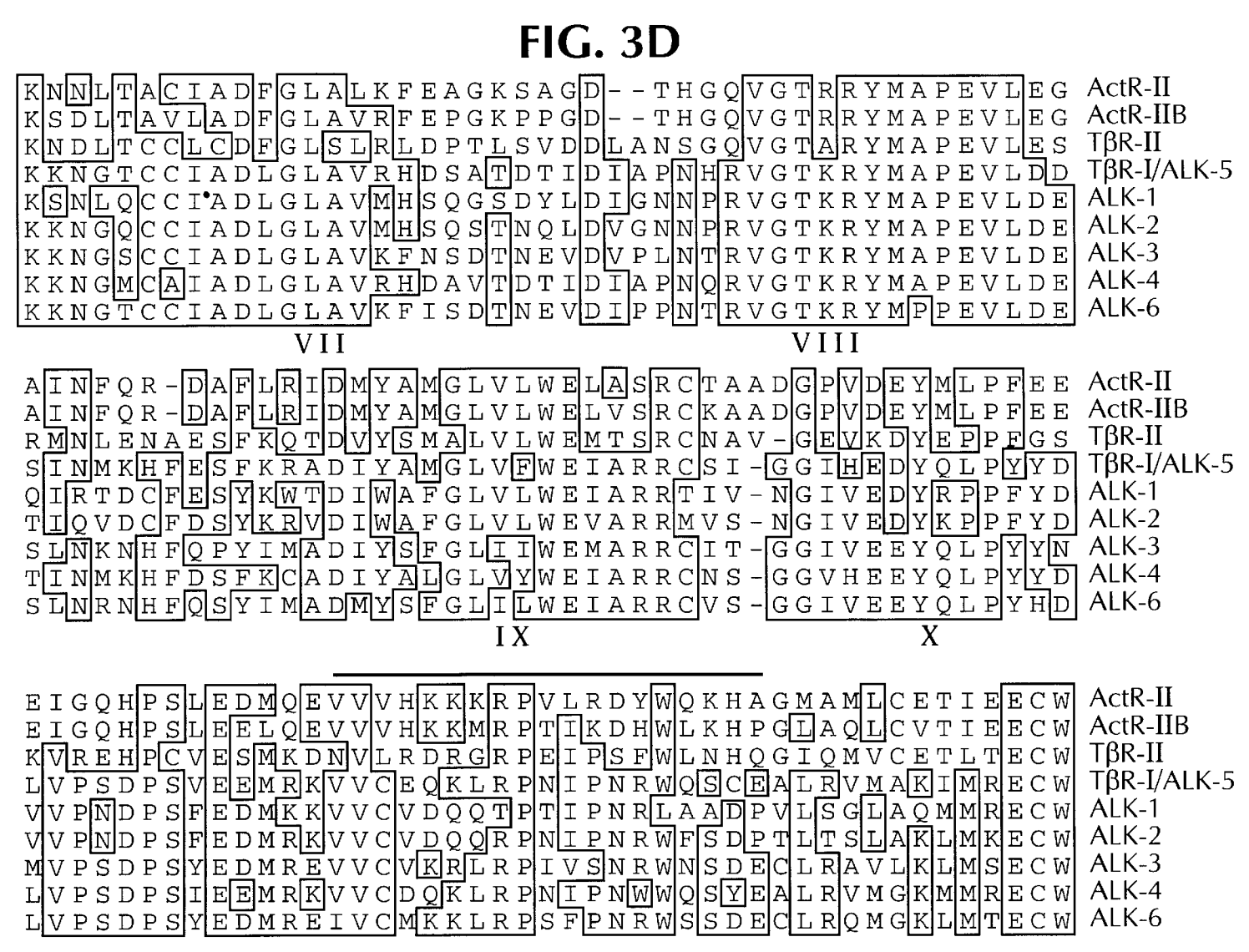
Figure 4:
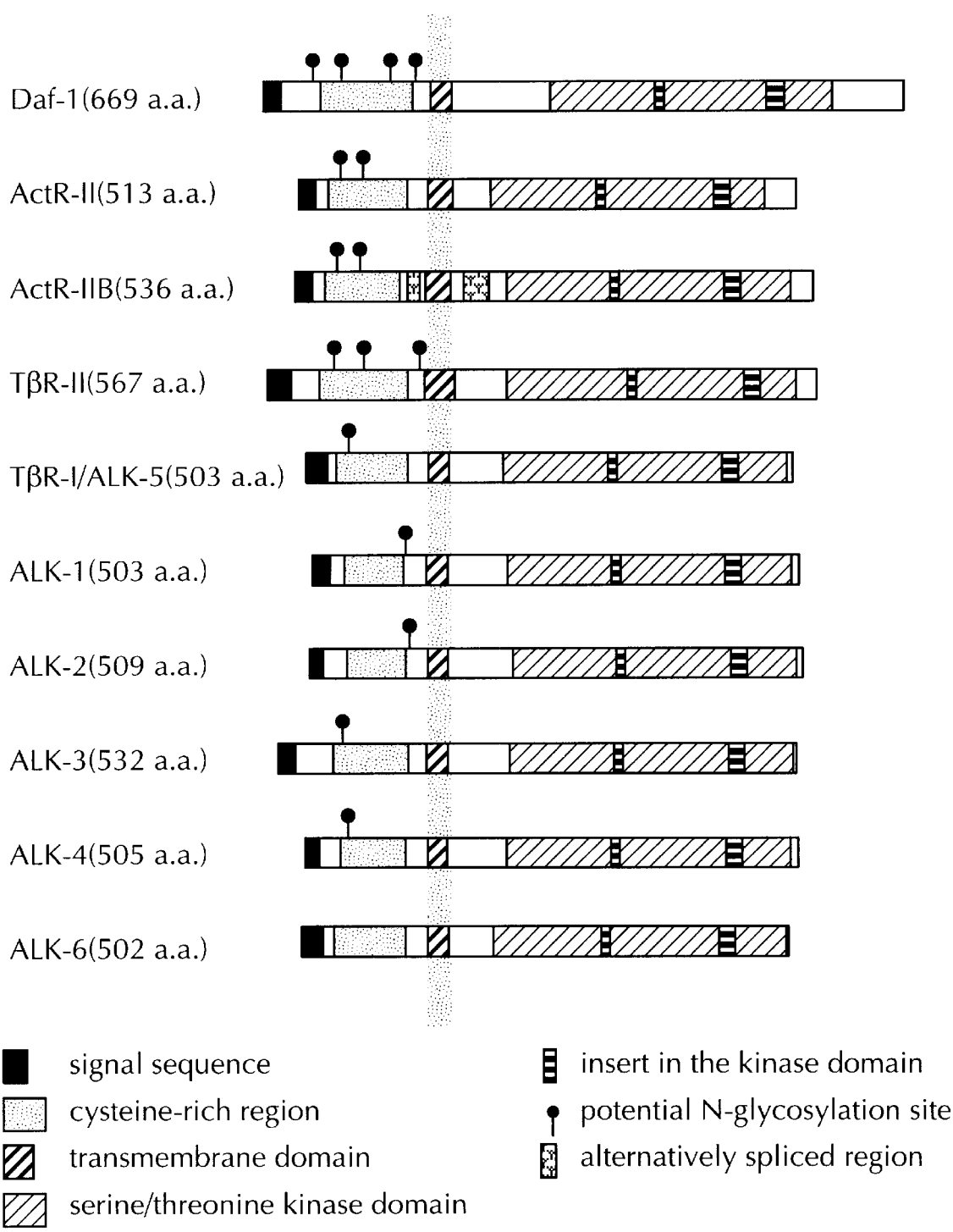
FIG. 4 shows, schematically, the structures for Daf-1, Act R-II, Act R-IIB, TβR-II, TβR-I/ALK-5, ALK's -1, -2 (Act RIA), -3, -4 (Act RIB) & -6.

The sequence alignment between the 6 ALK genes and TβR-II, mActR-II and ActR-IIB is shown in FIG. 3. These molecules have a similar domain structure; an N-terminal predicted hydrophobic signal sequence (von Heijne (1986) Nucl. Acids Res. 14: 4683–4690) is followed by a relatively small extracellular cysteine-rich ligand binding domain, a single hydrophobic transmembrane region (Kyte & Doolittle (1982) J. Mol. Biol. 157, 105–132) and a C-terminal intracellular portion, which consists almost entirely of a kinase domain (FIGS. 3 and 4).

The extracelluar domains of these receptors have cysteine-rich regions, but they show little sequence similarity; for example, less than 20% sequence identity is found between Daf-1, ActR-II, TβR-II and ALK-5. The ALKs appear to form a subfamily as they show higher sequence similarities (15–47% identity) in their extracellular domains. The extracellular domains of ALK-5 and ALK-4 have about 29% sequence identity. In addition, ALK-3 and ALK-6 share a high degree of sequence similarity in their extracellular domains (46% identity).

The positions of many of the cysteine residues in all receptors can be aligned, suggesting that the extracellular domains may adopt a similar structural configuration. See FIG. 5 for ALKs-1, -2, -3 &-5. Each of the ALKs (except ALK-6) has a potential N-linked glycosylation site, the position of which is conserved between ALK-1 and ALK-2, and between ALK-3, ALK-4 and ALK-5 (see FIG. 4).

Figures 6, 7:
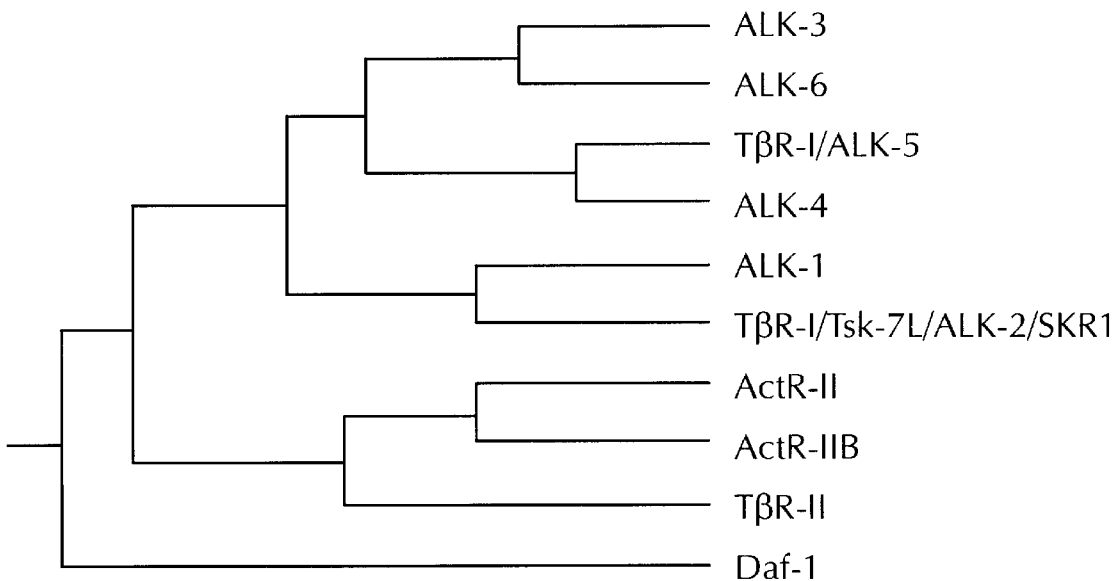
FIG. 6 is a comparison of kinase domains of serine/threonine kinases, showing the percentage amino-acid identity of the kinase domains.
FIG. 7 shows the pairwise alignment relationship between the kinase domains of the receptor serine/threonine kinases. The dendrogram was generated using the Jotun-Hein alignment program (Hein (1990) Meth. Enzymol. 183, 626–645).

The sequence similarities in the kinase domains between daf-1, ActR-II, TβR-II and ALK-5 are approximately 40%, whereas the sequence similarity between the ALKs 1 to 6 is higher (between 59% and 90%; see FIG. 6). Pairwise comparison using the Jutun-Hein sequence alignment program (Hein (1990) Meth, Enzymol., 183, 626–645), between all family members, identifies the ALKs as a separate subclass among serine/threonine kinases (FIG. 7).

The catalytic domains of kinases can be divided into 12 subdomains with stretches of conserved amino-acid residues. The key motifs are found in serine/threonine kinase receptors suggesting that they are functional kinases. The consensus sequence for the binding of ATP (Gly-X-Gly-X-X-Gly, SEQ ID NO. 26, in subdomain I followed by a Lys residue further downstream in subdomain II) is found in all the ALKs.

The kinase domains of daf-1, ActR-II, and ALKs show approximately equal sequence similarity with tyrosine and serine/threonine protein kinases. However analysis of the amino-acid sequences in subdomains VI and VIII, which are the most useful to distinguish a specificity for phosphorylation of tyrosine residues versus serine/threonine residues (Hanks et al (1988) Science 241 42–52) indicates that these kinases are serine/threonine kinases; refer to Table 2.

| KINASE | SUBDOMAINS | |
|---|---|---|
| | VIB | VIII |
| Serine/threonine kinase consensus | DLKPEN SEQ ID NO: 38 | G (T/S) XX (Y/F) X SEQ ID NO: 43 |
| Tyrosine kinase consensus | DLAARN SEQ ID NO: 39 | XP(I/V) (K/R) W (T/M) SEQ ID NO:44 |
| Act R-II | DIKSKN SEQ ID NO: 40 | GTRRYM SEQ ID NO:45 |
| Act R-IIB | DFKSKN SEQ ID NO: 41 | GTRRYM SEQ ID NO:45 |
| TβR-II | DLKSSN SEQ ID NO: 42 | GTARYM SEQ ID NO:46 |
| ALK-I | DFKSRN SEQ ID NO: 27 | GTKRYM SEQ ID NO: 29 |
| ALK -2, -3, -4, -5, & -6 | DLKSKN SEQ ID NO: 28 | GTKRYM SEQ ID NO: 29 |

The sequence motifs DLKSKN (Subdomain VIB) and GTKRYM (Subdomain VIII), that are found it most of the serine/threonine kinase receptors, agree well with the consensus sequences for all protein serine/threbnine kinase receptors in these regions. In addition, these receptors, except for ALK-1, do not have a tyrosine residue surrounded by acidic residues between subdomains VII and VIII, which is common for tyrosine kinases. A unique characteristic of the members of the ALK serine/threonine kinase receptor family is the presence of two short inserts in the kinase domain between subdomains VIA and VIB and between subdomains X and XI. In the intracellular domain, these regions, together with the juxtamembrane part and C-terminal tail, are the most divergent between family members (see FIGS. 3 and 4). Based on the sequence similarity with the type II receptors for TGF-β and activin, the C termini of the kinase domains of ALKs-1 to -6 are set at Ser-495, Ser-501, Ser-527, Gln-500, Gln-498 and Ser-497, respectively.

mRNA Expression

The distribution of ALK-1, -2, -3, -4 was determined by Northern blot analysis. A Northern blot filter with mRNAs from different human tissues was obtained from Clontech (Palo Alto, Calif.). The filters were hybridized with $^{32}$P-labelled probes at 42° C. overnight in 50% formaldehyde, 5×standard saline citrate (SSC; 1×SSC is 50 mM sodium citrate, pH 7.0, 150 mM NaCl), 0.1% SDS, 50 mM sodium phosphate, 5×Denhardt's solution and 0.1 mg/ml salmon sperm DNA. In order to minimize cross-hybridization, probes were used that did not encode part of the kinase domains, but corresponded to the highly diverged sequences of either 5' untranslated and ligand-binding regions (probes for ALK-1, -2 and -3) or 3' untranslated sequences (probe for ALK-4). The probes were labelled by random priming using the Multiprime (or Mega-prime) DNA labelling system and [α-$^{32}$P] dCTP (Feinberg & Vogelstein (1983) Anal. Biochem. 132: 6–13). Unincorporated label was removed by Sephadex G-25 chromatography. Filters were washed at 65° C., twice for 30 minutes in 2.5×SSC, 0.1% SDS and twice for 30 minutes in 0.3×SSC, 0.1% SDS before being exposed to X-ray film. Stripping of blots was performed by incubation at 90–100° C. in water for 20 minutes.

Our further analysis suggest ALK-1 is endothelial cell specific.

The ALK-5 mRNA size and distribution were determined by Northern blot analysis as above. An EcoR1 fragment of 980 bp of the full length ALK-5 cDNA clone, corresponding to the C-terminal part of the kinase domain and 3' untranslated region (nucleotides 1259–2232 in SEQ ID No. 9) was used as a probe. The filter was washed twice in 0.5×SSC, 0.1% SDS at 550° C. for 15 minutes.

Using the probe for ALK-1, two transcripts of 2.2 and 4.9 kb were detected. The ALK-1 expression level varied strongly between different tissues, high in placenta and lung, moderate in heart, muscle and kidney, and low (to not detectable) in brain, liver and pancreas. The relative ratios between the two transcripts were similar in most tissues; in kidney, however, there was relatively more of the 4.9 kb transcript. By reprobing the blot with a probe for ALK-2, one transcript of 4.0 kb was detected with a ubiquitous expression pattern. Expression was detected in every tissue investigated and was highest in placenta and skeletal muscle. Subsequently the blot was reprobed for ALK-3. One major transcript of 4.4 kb and a minor transcript of 7.9 kb were detected. Expression was high in skeletal muscle, in which also an additional minor transcript of 10 kb was observed. Moderate levels of ALK-3 mRNA were detected in heart, placenta, kidney and pancreas, and low (to not detectable) expression was found in brain, lung and liver. The relative ratios between the different transcripts were similar in the tested tissues, the 4.4 kb transcript being the predominant one, with the exception for brain where both transcripts were expressed at a similar level. Probing the blot with ALK-4 indicated the presence of a transcript with the estimated size of 5.2 kb and revealed an ubiquitous expression pattern. The results of Northern blot analysis using the probe for ALK-5 showed that a 5.5 kb transcript is expressed in all human tissues tested, being most abundant in placenta and least abundant in brain and heart.

The distribution of mRNA for mouse ALK-3 and -6 in various mouse tissues was also determined by Northern blot analysis. A multiple mouse tissue blot was obtained from Clontech, Palo Alto, Calif., U.S.A. The filter was hybridized as described above with probes for mouse ALK-3 and ALK-6. The EcoRI-PstI restriction fragment, corresponding to nucleotides 79–1100 of ALK-3, and the SacI-HpaI fragment, corresponding to nucleotides 57–720 of ALK-6, were used as probes. The filter was washed at 65° C. twice for 30 minutes in 2.5×SSC, 0.1% SDS and twice for 30 minutes with 0.3×SSC, 0.1% SDS and then subjected to autoradiography.

Using the probe for mouse ALK-3, a 1.1 kb transcript was found only in spleen. By reprobing the blot with the ALK-6 specific probe, a transcript of 7.2 kb was found in brain and a weak signal was also seen in lung. No other signal was seen in the other tissues tested, i.e. heart, liver, skeletal muscle, kidney and testis.

All detected transcript sizes were different, and thus no cross-reaction between mRNAs for the different ALKs was observed when the specific probes were used. This suggests that the multiple transcripts of ALK-1 and ALK-3 are coded from the same gene. The mechanism for generation of the different transcripts is unknown at present; they may be formed by alternative mRNA splicing, differential polyadenylation, use of different promoters, or by a combination of these events. Differences in mRNA splicing in the regions coding for the extracellular domains may lead to the synthesis of receptors with different affinities for ligands, as was shown for mActR-IIB (Attisano et al (1992) Cell 68, 97–108) or to the production of soluble binding protein.

The above experiments describe the isolation of nucleic acid sequences coding for new family of human receptor kinases. The cDNA for ALK-5 was then used to determine the encoded protein size and binding properties.

Properties of the ALKs cDNA Encoded Proteins

To study the properties of the proteins encoded by the different ALK cDNAs, the cDNA for each ALK was subcloned into a eukaryotic expression vector and transfected into various cell types and then subjected to immunoprecipitation using a rabbit antiserum raised against a synthetic peptide corresponding to part of the intracellular juxtamembrane region. This region is divergent in sequence between the various serine/threonine kinase receptors. The following amino-acid residues were used:

| | |
|---|---|
| ALK-1 | 145–166 |
| ALK-2 | 151–172 |
| ALK-3 | 181–202 |
| ALK-4 | 153–171 |
| ALK-5 | 158–179 |
| ALK-6 | 151–168 |

The rabbit antiserum against ALK-5 was designated VPN.

The peptides were synthesized with an Applied Biosystems 430A Peptide Synthesizer using t-butoxycarbonyl chemistry and purified by reversed-phase high performance liquid chromatography. The peptides were coupled to keyhole limpet haemocyanin (Calbiochem-Behring) using glutaraldehyde, as described by Guillick et al (1985) EMBO J. 4, 2869–2877. The coupled peptides were mixed with Freunds adjuvant and used to immunize rabbits.

Transient Transfection of the ALK-5 cDNA

COS-1 cells (American Type Culture Collection) and the R mutant of Mv1Lu cells (for references, see below) were cultured in Dulbecco's modified Eagle's medium containing 10% fetal bovine serum (FBS) and 100 units/ml penicillin and 50 µg lml streptomycin in 5% $CO_2$ atmosphere at 37° C. The ALK-5 cDNA (nucleotides (−76)–2232), which includes the complete coding region, was cloned in the pSV7d vector (Truett et al, (1985). DNA 4, 333–349), and used for transfection. Transfection into COS-1 cells was performed by the calcium phosphate precipitation method (Wigler et al (1979) Cell 16, 777–785). Briefly, cells were seeded into 6-well cell culture plates at a density of 5×10$^5$ cells/well, and transfected the following day with 10 µg of recombinant plasmid. After overnight incubation, cells were washed three times with a buffer containing 25 mM Tris-HCl, pH 7.4, 138 mM NaCl, 5 mM KCl, 0.7 mM $CaCl_2$, 0.5 mM $MgCl_2$ and 0.6 mM $Na_2HPO_4$, and then incubated with Dulbecco's modified Eagle's medium containing FBS and antibiotics. Two days after transfection, the cells were metabolically labelled by incubating the cells for 6 hours in methionine and cysteine-free MCDB 104 medium with 150 µCi/ml of [$^{35}$S]-methionine and [$^{35}$S]-cysteine (in vivo labelling mix; Amersham). After labelling, the cells were washed with 150 mM NaCl, 25 mM Tris-HCl, pH 7.4, and then solubilized with a buffer containing 20 mM Tris-HCl, pH 7.4, 150 mM NaCl, 10 mM EDTA, 1% Triton X-100, 1% deoxycholate, 1.5% Trasylol (Bayer) and 1 mM phenylmethylsulfonylfluoride (PMSF; Sigma). After 15 minutes on ice, the cell lysates were pelleted by centrifugation, and the supernatants were then incubated with 7 µl of preimmune serum for 1.5 hours at 4° C. Samples were then given 50 µl of protein A-Sepharose (Pharmacia-LKB) slurry (50% packed beads in 150 mM NaCl, 20 mM Tris-HCl, pH 7.4, 0.2% Triton X100) and incubated for 45 minutes at 4° C. The beads were spun down by centrifugation, and the supernatants (1 ml) were then incubated with either 7 µl of preimmune serum or the VPN antiserum for 1.5 hours at 4° C. For blocking, 10 µg of peptide was added together with the antiserum. Immune complexes were then given 50 µl of protein A-Sepharose (Pharmacia-LKB) slurry (50% packed beads in 150 mM NaCl, 20 mM Tris-HCl, pH 7.4, 0.2% Triton X-100) and incubated for 45 minutes at 4° C. The beads were spun down and washed four times with a washing buffer (20 mM Tris-HCl, pH 7.4, 500 mM NaCl, 1% Triton X-100, 1% deoxycholate and 0.2% SDS), followed by one wash in distilled water. The immune complexes were eluted by boiling for 5 minutes in the SDS-sample buffer (100 mM Tris-HCl, pH 8.8, 0.01% bromophenol blue, 36% glycerol, 4% SDS) in the presence of 10 mM DTT, and analyzed by SDS-gel electrophoresis using 7–15% polyacrylamide gels (Blobel and Dobberstein, (1975) J. Cell Biol. 67, 835–851). Gels were fixed, incubated with Amplify (Amersham) for 20 minutes, and subjected to fluorography. A component of 53 Da was seen. This component was not seen when preimmune serum was used, or when 10 µg blocking peptide was added together with the antiserum. Moreover, it was not detectable in samples derived from untransfected COS-1 cells using either preimmune serum or the antiserum.

Digestion with Endoglycosidase F

Samples immunoprecipitated with the VPN antisera obtained as described above were incubated with 0.5 U of endoglycosidase F (Boehringer Mannheim Biochemica) in a buffer containing 100 mM sodium phosphate, pH 6.1, 50 mM EDTA, 1% Triton X-100, 0.1% SDS and 1% β-mercaptoethanol at 37° C. for 24 hours. Samples were eluted by boiling for 5 minutes in the SDS-sample buffer, and analyzed by SDS-polyacrylamide gel electrophoresis as described above. Hydrolysis of N-linked carbohydrates by endoglycosidase F shifted the 53 kDa band to 51 kDa. The extracelluar domain of ALK-5 contains one potential acceptor site for N-glycosylation and the size of the deglycosylated protein is close to the predicted size of the core protein.

Establishment of PAE Cell Lines Expressing ALK-5

In order to investigate whether the ALK-5 cDNA encodes a receptor for TGF-β, porcine aortic endothelial (PAE) cells were transfected with an expression vector containing the ALK-5 cDNA, and analyzed for the binding of $^{125}$I-TGF-β1.

PAE cells were cultured in Ham's F-12 medium supplemented with 10% FBS and antibiotics (Miyazono et al., (1988) J. Biol. Chem. 263, 6407–6415). The ALK-5 cDNA was cloned into the cytomegalovirus (CMV)-based expression vector pcDNA I/NEO (Invitrogen), and transfected into PAE cells by electroporation. After 48 hours, selection was initiated by adding Geneticin (G418 sulphate; Gibco-BRL) to the culture medium at a final concentration of 0.5 mg/ml (Westermark et al., (1990) Proc. Natl. Acad. Sci. USA 87, 128–132). Several clones were obtained, and after analysis by immunoprecipitation using the VPN antiserum, one clone denoted PAE/TβR-1 was chosen and further analyzed.

Iodination of TGF-β1, Binding and Affinity Crosslinking

Recombinant human TGF-β1 was iodinated using the chloramine T method according to Frolik et al., (1984) J. Biol. Chem. 259, 10995–11000. Cross-linking experiments were performed as previously described (Ichijo et al., (1990) Exp. Cell Res. 187, 263–269). Briefly, cells in 6-well plates were washed with binding buffer (phosphate-buffered saline containing 0.9 mM $CaCl_2$, 0.49 mM $MgCl_2$ and 1 mg/ml bovine serum albumin (BSA)), and incubated on ice in the same buffer with $^{125}$T-TGF-β1 in the presence or absence of excess unlabelled TGF-β1 for 3 hours. Cells were washed and cross-linking was done in the binding buffer without BSA together with 0.28 mM disuccinimidyl suberate (DSS; Pierce Chemical Co.) for 15 minutes on ice. The cells were harvested by the addition of 1 ml of detachment buffer (10 mM Tris-HCl, pH 7.4, 1 mM EDTA, 10% glycerol, 0.3 mM PMSF). The cells were pelleted by centrifugation, then resuspended in 50 μl of solubilization buffer (125 mM NaCl, 10 mM Tris-HCl, pH 7.4, 1 mM EDTA, 1% Triton X-100, 0.3 mM PMSF, 1% Trasylol) and incubated for 40 minutes on ice. Cells were centrifuged again and supernatants were subjected to analysis by SDS-gel electrophoresis using 4–15% polyacrylamide gels, followed by autoradiography. $^{125}$I-TGF-β1 formed a 70 kDa cross-linked complex in the transfected PAE cells (PAE/TβR-I cells). The size of this complex was very similar to that of the TGF-β type I receptor complex observed at lower amounts in the untransfected cells. A concomitant increase of 94 kDa TGF-β type II receptor complex could also be observed in the PAE/TβR-I cells. Components of 150–190 kDa, which may represent crosslinked complexes between the type I and type II receptors, were also observed in the PAE/TβR-I cells.

In order to determine whether the cross-linked 70 kDa complex contained the protein encoded by the ALK-5 cDNA, the affinity cross-linking was followed by immunoprecipitation using the VPN antiserum. For this, cells in 25 $cm^2$ flasks were used. The supernatants obtained after cross-linking were incubated with 7 μl of preimmune serum or VPN antiserum in the presence or absence of 10 μg of peptide for 1.5 h at 4° C. Immune complexes were then added to 50 μl of protein A-Sepharose slurry and incubated for 45 minutes at 4° C. The protein A-Sepharose beads were washed four times with the washing buffer, once with distilled water, and the samples were analyzed by SDS-gel electrophoresis using 4–15% polyacrylamide gradient gels and autoradiography. A 70 kDa cross-linked complex was precipitated by the VPN antiserum in PAE/TβR-1 cells, and a weaker band of the same size was also seen in the untransfected cells, indicating that the untransfected PAE cells contained a low amount of endogenous ALK-5. The 70 kDa complex was not observed when preimmune serum was used, or when immune serum was blocked by 10 μg of peptide. Moreover, a coprecipitated 94 kDa component could also be observed in the PAE/TβR-I cells. The latter component is likely to represent a TGF-β type II receptor complex, since an antiserum, termed DRL, which was raised against a synthetic peptide from the C-terminal part of the TGF-β type II receptor, precipitated a 94 kDa TGF-β type II receptor complex, as well as a 70 kDa type I receptor complex from PAE/TβR-I cells.

The carbohydrate contents of ALK-5 and the TGF-β type II receptor were characterized by deglycosylation using endoglycosidase F as described above and analyzed by SDS-polyacrylamide gel electrophoresis and autoradiography. The ALK-5 cross-linked complex shifted from 70 kDa to 66 kDa, whereas that of the type II receptor shifted from 94 kDa to 82 kDa. The observed larger shift of the type II receptor band compared with that of the ALK-5 band is consistent with the deglycosylation data of the type I and type II receptors on rat liver cells reported previously (Cheifetz et al (1988) J. Biol. Chem. 263, 16984–16991), and fits well with the fact that the porcine TGF-β type II receptor has two N-glycosylation sites (Lin et al (1992) Cell 68, 775–785), whereas ALK-5 has only one (see SEQ ID No. 9).

Binding of TGF-β1 to the type I receptor is known to be abolished by transient treatment of the cells with dithiothreitol (DTT) (Cheifetz and Massague. (1991) J. Biol. Chem. 266, 20767–20772; Wrana et al (1992) Cell 71, 1003–1014). When analyzed by affinity cross-linking, binding of $^{125}$I-TGF-β1 to ALK-5, but not to the type II receptor, was completely abolished by DTT treatment of PAE/TβR-1 cells. Affinity cross-linking followed by immunoprecipitation by the VPN antiserum showed that neither the ALK-5 nor the type II receptor complexes was precipitated after DTT treatment, indicating that the VPN antiserum reacts only with ALK-5. The data show that the VPN antiserum recognizes a TGF-β type I receptor, and that the type I and type II receptors form a heteromeric complex.

$^{125}$I-TGF-β1 Binding & Affinity Crosslinking of Transfected COS Cells

Transient expression plasmids of ALKs-1 to -6 and TβR-II were generated by subcloning into the pSV7d expression vector or into the pcDNA I expression vector (Invitrogen). Transient transfection of COS-1 cells and iodination of TGF-β1 were carried out as described above. Crosslinking and immunoprecipitation were performed as described for PAE cells above.

Transfection of cDNAs for ALKs into COS-1 cells did not show any appreciable binding of $^{125}$I-TGFβ1, consistent with the observation that type I receptors do not bind TGF-β in the absence of type II receptors. When the TβR-II cDNA was co-transfected with cDNAs for the different ALKs, type I receptor-like complexes were seen, at different levels, in each case. COS-1 cells transfected with TβR-II and ALK cDNAs were analyzed by affinity crosslinking followed by immunoprecipitation using the DRL antisera or specific antisera against ALKs. Each one of the ALKs bound $^{125}$I-TGF-β1 and was coimmunoprecipitated with the TβR-II complex using the DRL antiserum. Comparison of the efficiency of the different ALKs to form heteromeric complexes with TβR-II, revealed that ALK-5 formed such complexes more efficiently than the other ALKs. The size of the crosslinked complex was larger for ALK-3 than for other ALKS, consistent with its slightly larger size.

Expression of the ALK Protein in Different Cell Types

Two different approaches were used to elucidate which ALK's are physiological type I receptors for TGF-β.

Firstly, several cell lines were tested for the expression of the ALK proteins by cross-linking followed by immunoprecipitation using the specific antiseras against ALKs and the TGF-β type II receptor. The mink lung epithelial cell line, Mv1Lu, is widely used to provide target cells for TGF-β action and is well, characterized regarding TGF-β receptors (Laiho et al (1990) J. Biol. Chem. 265, 18518–18524; Laiho et al (1991) J. Biol. Chem. 266, 9108–9112). Only the VPN antiserum efficiently precipitated both type I and type II TGF-β receptors in the wild type Mv1Lu cells. The DRL antiserum also precipitated components with the same size as those precipitated by the VPN antiserum. A mutant cell line (R mutant) which lacks the TGF-β type I receptor and does not respond to TGF-β (Laiho et al, supra) was also investigated by cross-linking followed by immunoprecipitation. Consistent with the results obtained by Laiho et al (1990), supra the type III and type II TGF-β receptor complexes, but not the type I receptor complex, were observed by affinity crosslinking. Crosslinking followed by immunoprecipatition using the DRL antiserum revealed only the type II receptor complex, whereas neither the type I nor type II receptor complexes was seen using the VPN antiserum. When the cells were metabolically labelled and subjected to immunoprecipitation using the VPN antiserum, the 53 kDa ALK-5 protein was precipitated in both the wild-type and R mutant Mv1Lu cells. These results suggest that the type I receptor expressed in the R mutant is ALK-5, which has lost the affinity for binding to TGF-β after mutation.

The type I and type II TGF-β receptor complexes could be precipitated by the VPN and DRL antisera in other cell lines, including human foreskin fibroblasts (AG1518), human lung adenocarcinoma cells (A549), and human oral squamous cell carcinoma cells (HSC-2). Affinity cross-linking studies revealed multiple TGF-β type I receptor-like complexes of 70–77 kDa in these cells. These components were less efficiently competed by excess unlabelled TGF-β1 in HSC-2 cells. Moreover, the type II receptor complex was low or not detectable in A549 and HSC-2 cells. Cross-linking followed by immunoprecipitation revealed that the VPN antiserum precipitated only the 70 kDa complex among the 70–77 kDa components. The DRL antiserum precipitated the 94 kDa type II receptor complex as well as the 70 kDa type I receptor complex in these cells, but not the putative type I receptor complexes of slightly larger sizes. These results suggest that multiple type I TGF-β receptors may exist and that the 70 kDa complex containing ALK-5 forms a heteromeric complex with the TGF-β type II receptor cloned by Lin et al (1992) Cell 68, 775–785, more efficiently that the other species. In rat pheochromocytoma cells (PC12) which have been reported to have no TGF-β receptor complexes by affinity cross-linking (Massagué et al (1990) Ann. N.Y. Acad. Sci. 593, 59–72), neither VPN nor DRL antisera precipitated the TGF-β receptor complexes. The antisera against ALKs-1 to -4 and ALK6 did not efficiently immunoprecipitate the crosslinked receptor complexes in porcine aortic endothelial (PAE) cells or human foreskin fibroblasts.

Next, it was investigated whether ALKs could restore responsiveness to TGF-β in the R mutant of Mv1Lu cells, which lack the ligand-binding ability of the TGF-β type I receptor but have intact type II receptor. Wild-type Mv1Lu cells and mutant cells were transfected with ALK cDNA and were then assayed for the production of plasminogen activator inhibitor-1 (PAI-1) which is produced as a result of TGF-β receptor activation as described previously by Laiho et al (1991) Mol. Cell Biol. 11, 972–978. Briefly, cells were added with or without 10 ng/ml of TGF-β1 for 2 hours in serum-free MCDB 104 without methionine. Thereafter, cultures were labelled with [$^{35}$S] methionine (40 μCi/ml) for 2 hours. The cells were removed by washing on ice once in PBS, twice in 10 mM Tris-HCl (pH 8.0), 0.5% sodium deoxycholate, 1 mM PMSF, twice in 2 mM Tris-HCl (pH 8.0), and once in PBS. Extracellular matrix proteins were extracted by scraping cells into the SDS-sample buffer containing DTT, and analyzed by SDS-gel electrophoresis followed by fluorography using Amplify. PAI-1 can be identified as a characteristic 45 kDa band (Laiho et al (1991) Mol. Cell Biol. 11, 972–978). Wild-type Mv1Lu cells responded to TGF-β and produced PAI-1, whereas the R mutant clone did not, even after stimulation by TGF-β1. Transient transfection of the ALK-5 cDNA into the R mutant clone led to the production of PAI-1 in response to the stimulation by TGF-β1, indicating that the ALK-5 cDNA encodes a functional TGF-β type I receptor. In contrast, the R mutant cells that were transfected with other ALKs did not produce PAI-1 upon the addition of TGF-β1.

Using similar approaches as those described above for the identification of TGF-β-binding ALKs, the ability of ALKs to bind activin in the presence of ActRII was examined. COS-1 cells were co-transfected as described above. Recombinant human activin A was iodinated using the chloramine T method (Mathews and Vale (1991) Cell 65, 973–982). Transfected COS-1 cells were analysed for binding and crosslinking of $^{125}$I-activin A in the presence or absence of excess unlabelled activin A. The crosslinked complexes were subjected to immunoprecipitation using DRL antisera or specific ALK antisera.

All ALKs appear to bind activin A in the presence of Act R-II. This is more clearly demonstrated by affinity cross-linking followed by immunopreciptation. ALK-2 and ALK-4 bound $^{125}$I-activin A and were coimmunoprecipitated with ActR-II. Other ALKs also bound $^{125}$I-activin A but with a lower efficiency compared to ALK-2 and ALK-4.

In order to investigate whether ALKs are physiological activin type I receptors, activin responsive cells were examined for the expression of endogenous activin type I receptors. Mv1Lu cells, as well as the R mutant, express both type I and type II receptors for activin, and the R mutant cells produce PAI-1 upon the addition of activin A. Mv1Lu cells were labeled with $^{125}$I-activin A, cross-linked and immunoprecipitated by the antisera against ActR-II or ALKs as described above.

The type I and type II receptor complexes in Mv1Lu cells were immunoprecipitated only by the antisera against ALK-2, ALK-4 and ActR-II. Similar results were obtained using the R mutant cells. PAE cells do not bind activin because of the lack of type II receptors for activin, and so cells were transfected with a chimeric receptor, to enable them to bind activin, as described herein. A plasmid (chim A) containing the extracelluar domain and C-terminal tail of Act R-II (amino-acids −19 to 116 and 465 to 494, respectively (Mathews and Vale (1991) Cell, 65, 973–982)) and the kinase domain of TβR-II (amino-acids 160–543) (Lin et al (1992) Cell, 68, 775–785) was constructed and transfected into pcDNA/neo (Invitrogen). PAE cells were stably transfected with the chim A plasmid by electroporation, and cells expressing the chim A protein were established as described previously. PAE/Chim A cells were then subjected to $^{125}$I-activin A labelling crosslinking and immunoprecipitation as described above.

Similar to Mv1Lu cells, activin type I receptor complexes in PAE/Chim A cells were immunoprecipitated by the ALK-2 and ALK-4 antisera. These results show that both ALK-2 and ALK-4 serve as high affinity type I receptors for activin A in these cells.

ALK-1, ALK-3 and ALK-6 bind TGF-β1 and activin A in the presence of their respective type II receptors, but the functional consequences of the binding of the ligands remains to be elucidated.

The experiments described supra suggested further experiments. Specifically, it is known that TGF-β family members acts as ligands in connection with specific type I and type II receptors, with resulting complexes interacting with members of the Smad family. See Heldin et al., Nature 390: 465–471 (1997), incorporated by reference. The Smad molecules are homologs of molecules found in Drosophila ("Mad"), and *C. elegans* (Sma), hence, the acronym "Smad". These are involved in signal transduction pathways downstream of serine/threonine kinase receptors. See Massagué et al., Trends Cell Biol. 2: 187–192 (1997). The different members of the family have different signaling roles. Smad1, for example, as well as Smad 2 and 3, and perhaps Smad 5, became phosphorylated via specific type 1 serine/threonine kinase receptors, and act in pathway restricted fashion. For example, Xenopus Mad1 induces ventral mesoderm, in the presence of BMP. The human Smad1 has been shown to have ventralizing activity. See Liu et al., Nature 381: 620–623 (1996); Kretzschmer et al., Genes Dev 11: 984–995 (1997). There is also some evidence that TGF-β phosphorylates Smad1. See Lechleider et al., J. Biol. Chem. 271: 17617–17620 (1996); Yingling et al., Proc. Natl. Acad. Sci. USA 93: 8940–8944 (1996). Given what was known regarding this complex signaling pathway, the role of ALK-1 was studied.

COS-7 cells, which do not express ALK-1, were transfected with cDNA encoding tagged ALK-1. The tag was hemagluttinin (hereafter "HA"), and a commercially available lipid containing transfecting agent was used. In parallel experiments, porcine aortic endothelial (PAE) cells were also used, because these cells express TGFβ type II receptors, and ALK-5, but not ALK-1. Hence, PAE cells were either transfected, or not. Transfection protocols are given, supra.

The cells were then contacted with $^{125}$I labelled TGF-β1, and were then contacted with ALK-1 specific antisera, to ascertain whether cross linking had occurred. See the experiments, supra, as well as ten Dijke et al., Science 264: 101–104 (1994), incorporated by reference. Antisera to ALK-5 were also used.

The results indicated that the ALK-1 antiserum immunoprecipitated complexes of the appropriate size from the transfected COS-7 and PAE cells, but not those which were not transfected, thereby establishing that ALK-1 is a receptor for TGF-β.

This was confirmed in experiments on human umbilical vein endothelial cells (HUVEC). These cells are known to express ALK-1 endogenously, as well as ALK-5. The ALK-5 antiserum and the ALK-1 antiserum both immunoprecipitated type I and type II receptor cross linked complexes. The ALK-1 antiserum immunoprecipitated band migrated slightly more slowly than the band immunprecipitated by the ALK-5 antiserum (see, e.g., FIG. 8). This is in agreement with the difference in size of ALK-1 and ALK-5, and it indicates that both ALK-1 and ALK-5 bind TGF-β in HUVECS.

Further, it shows that ALK-1 acts as a co-called "type I" TGF-β receptor in an endogenous, physiological setting.

Once it was determined that TGF-β and ALK-1 interact, studies were carried out to determine whether or not activation of ALK-1 resulted in phosphorylation of Smads. To test this, COS-7 cells were transfected in the same manner described supra with either Flag tagged Smad1, Flag tagged Smad2 or Flag tagged Smad-5 together with either a constitutively active form of ALK-1, or a constitutively active form of ALK-5. Specifically, the variant of ALK-1 is Q201D, and that of ALK-5 is T204D. Constitutively active ALK-1 was used to avoid the need for an additional transfection step. To elaborate, it is known that for the TGF-β pathway to function adequately, a complex of two, type I receptors, and two, type II receptors must interact, so as to activate the receptors. Constitutively active receptors, such as what was used herein, do not require the presence of the type II receptor to function. See Wieser et al., EMBO J 14: 2199–2208 (1995). In order to determine if the resulting transfected cells produced phosphorylated Smads, Smads were determined using a Flag specific antibody, which precipitated them, and phosphorylation was determined using the antiphosphoserine antibody of Nishimura et al., J. Biol. Chem. 273: 1872–1879 (1998). It was determined, when the data were analyzed, that Smad1 and Smad-5 (an intracellular signalling molecule which is structurally highly similar to Smad1) were phosphorylated following interaction with activated ALK-1, but not following interaction of TGF-β and ALK-5. Conversely, the interaction of TGF-β and ALK-5 led to phosphorylation of Smad 2, but not Smad 1. This supports a conclusion that ALK-1 transduces signal in a manner similar to BMPs.

FIG. 8 depicts the phosphorylation of Smad-5 following interaction with ALK-1 but not ALK-5. Phosphorylation of both Smad-5 and Smad1 has been shown for BMP type I receptors suggesting ALK-1 is functionally very similar to ALK3 (BMPR-IA) and (ALK6 BMPR-IB).

Additional experiments were then carried out to study the interaction of ALK-1 with Smad-1. Specifically, COS-7 cells were transfected with cDNA which encoded the wild type form of the TGFβ type II receptor (TBR-II), a kinase inactive form of ALK-1, and Flag tagged Smad-1. Kinase inactive ALK-1 was used, because the interaction of Smad-1 and receptors is known to be transient, as once Smads are phosphorylated they dissociate from the type I receptor. See Marcias-Silva et al., Cell 87: 1215–1224 (1996); Nakao et al., EMBO J 16: 5353–5362 (1997). Affinity cross-linking, using $^{125}$I-TGF-β1, and immunoprecipitation with Flag antibody was carried out, as discussed supra. The expression of ALK-1 was determined using anti-HA antibody, since the vector used to express ALK-1 effectively tagged it with HA.

The immunoprecipitating of Smad1 resulted in coprecipitation of a cross linked TBR-II/ALK-1 complex, suggesting a direct association of Smad1 with ALK-1.

These examples show that one can identify molecules which inhibit, or enhance expression of a gene whose expression is regulated by phosphorylated Smad1. To elaborate, as ALK-1 has been identified as a key constituent of the pathway by which Smad1 is phosphorylated, one can contact cells which express both Smad1 and ALK-1 with a substance of interest, and then determine if the Smad1 becomes phosphorylated. The cells can be those which inherently express both ALK-1 and Smad1, or which have been transformed or transfected with DNA encoding one or both of these. One can determine the phosphorylation via, e.g., the use of anti phosphorylated serine antibodies, as discussed supra. In an especially preferred embodiment, the assay can be carried out using TGF-β, as a competing agent. The TGF-β, as has been shown, does bind to ALK-1, leading to phosphorylation of Smad1. Hence, by determining a value with TGF-β alone, one can then compare a value determined with amounts of the substance to be tested, in the presence of TGF-β. Changes in phosphorylation levels can thus be attributed to the test substance.

In this type of system, it must be kept in mind that both type I receptors and type II receptors must be present; however, as indicated, supra, one can eliminate the requirement for a type II receptor by utilizing a constitutively active form of ALK-1, such as the form described supra. Additional approaches to inhibiting this system will be clear to the skilled artisan. For example, since it is known that there is interaction between Smad1 and the ALK-1 receptor, one can test for inhibition via the use of small molecules which inhibit the receptor/Smad interaction. Heldin et al., supra, mention Smad6 and Smad7 as Smad1 inhibitors, albeit in the context of a different system. Hence one can test for inhibition, or inhibit the interaction, via adding a molecule to be tested or for actual inhibition to a cell, wherein the molecule is internalized by the cell, followed by assaying for phosphdrylation, via a method such as is discussed supra.

In a similar way, one can assay for inhibitors of type I/type II receptor interaction, by testing the molecule of interest in a system which includes both receptors, and then assaying for phorphorylation.

Conversely, activators or agonists can also be tested for, or utilized, following the same type of procedures.

Via using any of these systems, one can identify any gene or genes which are activated by phosphorylated Smad1. To elaborate, the art is very familiar with systems of expression analysis, such as differential display PCR, subtraction hybridization, and other systems which combine driver and testes populations of nucleic acids, whereby transcripts which are expressed or not expressed can be identified. By simply using an activator/inhibitor of the system disclosed herein, on a first sample, and a second sample where none is used, one can then carry out analysis of transcript, thereby determining the transcripts of interest.

Also a part of the invention is the regulation of a phosphorylation of Smad-1 or Smad-5, with inhibitors, such as antibodies against the extracellular domain of ALK-1 or TGF-β, or enhancers, such as TGF-β itself, or those portions of the TGF-β molecule which are necessary for binding. Indeed, by appropriate truncation, one can also determine what portions of ALK-1 are required for phosphorylation of Smad1 or Smad-5 to take place.

The invention has been described by way of example only, without restriction of its scope. The invention is defined by the subject matter herein, including the claims that follow the immediately following full Sequence Listings.

We claim:

1. A method for determining if a substance inhibits TGF-β/Alk1 induced Smad1 phosphorylation comprising contacting a first sample of cells that express an Alk1 and Smad1 with said substance in the presence of TGF-β and determining if Smad1 phosphorylation is inhibited, wherein a reduced level of phosphorylation in said first sample of cells contacted with said substance in the presence of TGF-β as compared to a control sample of cells is indicative of said substance inhibiting TGF-β/Alk-1 phosphorylation of Smad1.

2. The method of claim 1, wherein said substance is an antibody that binds to TGF-β.

3. The method of claim 1, wherein said substance is an antibody that binds to the extracellular domain of Alk-1.

4. The method of claim 1, wherein said first sample of cells that express Alk-1 are transfected with a nucleic acid molecule that encodes an Alk-1.

5. The method of claim 1, wherein said first sample of cells that express Alk-1 are transfected with a nucleic acid molecule which encodes a Smad1.

6. The method of claim 5, wherein said Smad1 is a Smad1 fusion polypeptide.

7. The method of claim 6, wherein said Smad1 is fused to Flag.

* * * * *

SEQUENCE LISTING

<160> NUMBER OF SEQ ID NOS: 46

<210> SEQ ID NO 1
<211> LENGTH: 1984
<212> TYPE: DNA
<213> ORGANISM: Homo sapiens

<400> SEQUENCE: 1

```
aggaaacggt ttattaggag ggagtggtgg agctgggcca ggcaggaaga cgctggaata      60
agaaacattt ttgctccagc ccccatccca gtcccgggag gctgccgcgc cagctgcgcc     120
gagcgagccc ctccccggct ccagcccggt ccggggccgc gccggacccc agcccgccgt     180
ccagcgctgg cggtgcaact gcggccgcgc ggtggagggg aggtggcccc ggtccgccga     240
aggctagcgc cccgccaccc gcagagcggg cccagaggga ccatgacctt gggctccccc     300
aggaaaggcc ttctgatgct gctgatggcc ttggtgaccc agggagaccc tgtgaagccg     360
tctcggggcc cgctggtgac ctgcacgtgt gagagcccac attgcaaggg gcctacctgc     420 cgggggggcct ggtgcacagt agtgctggtg cgggaggagg ggaggcaccc ccaggaacat     480
cggggctgcg ggaacttgca cagggagctc tgcagggggc gccccaccga gttcgtcaac     540
cactactgct gcgacagcca cctctgcaac cacaacgtgt ccctggtgct ggaggccacc     600
caacctcctt cggagcagcc gggaacagat ggccagctgg ccctgatcct gggccccgtg     660
ctggccttgc tggccctggt ggccctgggt gtcctgggcc tgtggcatgt ccgacggagg     720
caggagaagc agcgtggcct gcacagcgag ctgggagagt ccagtctcat cctgaaagca     780
tctgagcagg gcgacacgat gttgggggac ctcctggaca gtgactgcac cacagggagt     840
ggctcagggc tccccttcct ggtgcagagg acagtggcac ggcaggttgc cttggtggag     900
tgtgtgggaa aaggccgcta tggcgaagtg tggcgggggct tgtggcacgg tgagagtgtg     960
gccgtcaaga tcttctcctc gagggatgaa cagtcctggt tccgggagac tgagatctat    1020
aacacagtat tgctcagaca cgacaacatc ctaggcttca tcgcctcaga catgacctcc    1080
```

```
cgcaactcga gcacgcagct gtggctcatc acgcactacc acgagcacgg ctccctctac    1140
gactttctgc agagacagac gctggagccc catctggctc tgaggctagc tgtgtccgcg    1200
gcatgcggcc tggcgcacct gcacgtggag atcttcggta cacagggcaa accagccatt    1260
gcccaccgcg acttcaagag ccgcaatgtg ctggtcaaga gcaacctgca gtgttgcatc    1320
gccgacctgg gcctggctgt gatgcactca cagggcagcg attacctgga catcggcaac    1380
aacccgagag tgggcaccaa gcggtacatg gcacccgagg tgctggacga gcagatccgc    1440
acggactgct ttgagtccta caagtggact gacatctggg cctttggcct ggtgctgtgg    1500
gagattgccc gccggaccat cgtgaatggc atcgtggagg actatagacc cccttctat    1560 gatgtggtgc ccaatgaccc cagctttgag gacatgaaga aggtggtgtg tgtggatcag    1620 cagacccca ccatccctaa ccggctggct gcagacccgg tcctctcagg cctagctcag    1680
atgatgcggg agtgctggta cccaaacccc tctgcccgac tcaccgcgct gcggatcaag    1740
aagacactac aaaaaattag caacagtcca gagaagccta aagtgattca atagcccagg    1800
agcacctgat tcctttctgc ctgcaggggg ctgggggggt gggggggcagt ggatggtgcc    1860 ctatctgggt agaggtagtg tgagtgtggt gtgtgctggg gatgggcagc tgcgcctgcc    1920
tgctcggccc ccagcccacc cagccaaaaa tacagctggg ctgaaacctg aaaaaaaaaa    1980
aaaa                                                                  1984
```

<210> SEQ ID NO 2
<211> LENGTH: 503
<212> TYPE: PRT
<213> ORGANISM: Homo sapiens

<400> SEQUENCE: 2

```
Met Thr Leu Gly Ser Pro Arg Lys Gly Leu Leu Met Leu Leu Met Ala
1               5                   10                  15

Leu Val Thr Gln Gly Asp Pro Val Lys Pro Ser Arg Gly Pro Leu Val
            20                  25                  30

Thr Cys Thr Cys Glu Ser Pro His Cys Lys Gly Pro Thr Cys Arg Gly
        35                  40                  45

Ala Trp Cys Thr Val Val Leu Val Arg Glu Glu Gly Arg His Pro Gln
    50                  55                  60

Glu His Arg Gly Cys Gly Asn Leu His Arg Glu Leu Cys Arg Gly Arg
65                  70                  75                  80

Pro Thr Glu Phe Val Asn His Tyr Cys Cys Asp Ser His Leu Cys Asn
                85                  90                  95

His Asn Val Ser Leu Val Leu Glu Ala Thr Gln Pro Pro Ser Glu Gln
            100                 105                 110

Pro Gly Thr Asp Gly Gln Leu Ala Leu Ile Leu Gly Pro Val Leu Ala
        115                 120                 125

Leu Leu Ala Leu Val Ala Leu Gly Val Leu Gly Leu Trp His Val Arg
    130                 135                 140

Arg Arg Gln Glu Lys Gln Arg Gly Leu His Ser Glu Leu Gly Glu Ser
145                 150                 155                 160

Ser Leu Ile Leu Lys Ala Ser Glu Gln Gly Asp Thr Met Leu Gly Asp
                165                 170                 175

Leu Leu Asp Ser Asp Cys Thr Thr Gly Ser Gly Ser Gly Leu Pro Phe
            180                 185                 190

Leu Val Gln Arg Thr Val Ala Arg Gln Val Ala Leu Val Glu Cys Val
        195                 200                 205
```

```
Gly Lys Gly Arg Tyr Gly Glu Val Trp Arg Gly Leu Trp His Gly Glu
    210                 215                 220
Ser Val Ala Val Lys Ile Phe Ser Ser Arg Asp Glu Gln Ser Trp Phe
225                 230                 235                 240
Arg Glu Thr Glu Ile Tyr Asn Thr Val Leu Leu Arg His Asp Asn Ile
                245                 250                 255
Leu Gly Phe Ile Ala Ser Asp Met Thr Ser Arg Asn Ser Ser Thr Gln
            260                 265                 270
Leu Trp Leu Ile Thr His Tyr His Glu His Gly Ser Leu Tyr Asp Phe
        275                 280                 285
Leu Gln Arg Gln Thr Leu Glu Pro His Leu Ala Leu Arg Leu Ala Val
    290                 295                 300
Ser Ala Ala Cys Gly Leu Ala His Leu His Val Glu Ile Phe Gly Thr
305                 310                 315                 320
Gln Gly Lys Pro Ala Ile Ala His Arg Asp Phe Lys Ser Arg Asn Val
                325                 330                 335
Leu Val Lys Ser Asn Leu Gln Cys Cys Ile Ala Asp Leu Gly Leu Ala
            340                 345                 350
Val Met His Ser Gln Gly Ser Asp Tyr Leu Asp Ile Gly Asn Asn Pro
        355                 360                 365
Arg Val Gly Thr Lys Arg Tyr Met Ala Pro Glu Val Leu Asp Glu Gln
    370                 375                 380
Ile Arg Thr Asp Cys Phe Glu Ser Tyr Lys Trp Thr Asp Ile Trp Ala
385                 390                 395                 400
Phe Gly Leu Val Leu Trp Glu Ile Ala Arg Arg Thr Ile Val Asn Gly
                405                 410                 415
Ile Val Glu Asp Tyr Arg Pro Pro Phe Tyr Asp Val Val Pro Asn Asp
            420                 425                 430
Pro Ser Phe Glu Asp Met Lys Lys Val Val Cys Val Asp Gln Gln Thr
        435                 440                 445
Pro Thr Ile Pro Asn Arg Leu Ala Ala Asp Pro Val Leu Ser Gly Leu
    450                 455                 460
Ala Gln Met Met Arg Glu Cys Trp Tyr Pro Asn Pro Ser Ala Arg Leu
465                 470                 475                 480
Thr Ala Leu Arg Ile Lys Lys Thr Leu Gln Lys Ile Ser Asn Ser Pro
                485                 490                 495
Glu Lys Pro Lys Val Ile Gln
            500

<210> SEQ ID NO 3
<211> LENGTH: 2724
<212> TYPE: DNA
<213> ORGANISM: Homo sapiens

<400> SEQUENCE: 3
ctccgagtac cccagtgacc agagtgagag aagctctgaa cgagggcacg cggcttgaag      60
gactgtgggc agatgtgacc aagagcctgc attaagttgt acaatggtag atggagtgat     120
gattcttcct gtgcttatca tgattgctct cccctcccct agtatggaag atgagaagcc     180
caaggtcaac cccaaactct acatgtgtgt gtgtgaaggt ctctcctgcg gtaatgagga     240
ccactgtgaa ggccagcagt gcttttcctc actgagcatc aacgatggct ccacgtcta      300
ccagaaaggc tgcttccagg tttatgagca gggaaagatg acctgtaaga ccccgccgtc     360
ccctggccaa gctgtggagt gctgccaagg ggactggtgt aacaggaaca tcacggccca     420
```

```
gctgcccact aaaggaaaat ccttccctgg aacacagaat ttccacttgg aggttggcct        480
cattattctc tctgtagtgt tcgcagtatg tcttttagcc tgcctgctgg gagttgctct        540
ccgaaaattt aaaaggcgca accaagaacg cctcaatccc cgagacgtgg agtatggcac        600
tatcgaaggg ctcatcacca ccaatgttgg agacagcact ttagcagatt tattggatca        660
ttcgtgtaca tcaggaagtg gctctggtct ccttttctg gtacaaagaa cagtggctcg         720
ccagattaca ctgttggagt gtgtcgggaa aggcaggtat ggtgaggtgt ggaggggcag        780
ctggcaaggg gaaaatgttg ccgtgaagat cttctcctcc cgtgatgaga agtcatggtt        840
cagggaaacg gaattgtaca acactgtgat gctgaggcat gaaaatatct taggtttcat        900
tgcttcagac atgacatcaa gacactccag tacccagctg tggttaatta cacattatca        960
tgaaatggga tcgttgtacg actatcttca gcttactact ctggatacag ttagctgcct       1020
tcgaatagtg ctgtccatag ctagtggtct tgcacatttg cacatagaga tatttgggac       1080
ccaagggaaa ccagccattg cccatcgaga tttaaagagc aaaaatattc tggttaagaa       1140
gaatggacag tgttgcatag cagatttggg cctggcagtc atgcattccc agagcaccaa       1200
tcagcttgat gtggggaaca atccccgtgt gggcaccaag cgctacatgg cccccgaagt       1260
tctagatgaa accatccagg tggattgttt cgattcttat aaaagggtcg atatttgggc       1320
ctttggactt gttttgtggg aagtggccag gcggatggtg agcaatggta tagtggagga       1380
ttacaagcca ccgttctacg atgtggttcc caatgaccca agttttgaag atatgaggaa       1440
ggtagtctgt gtggatcaac aaaggccaaa catacccaac agatggttct cagacccgac       1500 attaaccctct ctggccaagc taatgaaaga atgctggtat caaaatccat ccgcaagact       1560
cacagcactg cgtatcaaaa agactttgac caaaattgat aattccctcg acaaattgaa       1620
aactgactgt tgacatttc atagtgtcaa gaggaagat ttgacgttgt tgtcattgtc         1680
cagctgggac ctaatgctgg cctgactggt tgtcagaatg gaatccatct gtctccctcc       1740
ccaaatggct gctttgacaa ggcagacgtc gtacccagcc atgtgttggg gagacatcaa       1800
aaccacccta acctcgctcg atgactgtga actgggcatt tcacgaactg ttcacactgc       1860
agagactaat gttggacaga cactgttgca aaggtaggga ctggaggaac acagagaaat       1920
cctaaaagag atctgggcat taagtcagtg gctttgcata gctttcacaa gtctcctaga       1980
cactccccac gggaaactca aggaggtggt gaatttttaa tcagcaatat tgcctgtgct       2040
tctcttcttt attgcactag gaattctttg cattccttac ttgcactgtt actcttaatt       2100
ttaaagaccc aacttgccaa aatgttggct gcgtactcca ctggtctgtc tttggataat       2160
aggaattcaa tttggcaaaa caaaatgtaa tgtcagactt tgctgcattt tacacatgtg       2220 ctgatgtta caatgatgcc gaacattagg aattgtttat acacaacttt gcaaattatt       2280
tattacttgt gcacttagta gttttttacaa aactgctttg tgcatatgtt aaagcttatt     2340
tttatgtggt cttatgattt tattacagaa atgtttttaa cactatactc taaaatggac      2400
attttctttt attatcagtt aaaatcacat tttaagtgct tcacatttgt atgtgtgtag       2460
actgtaactt ttttttcagtt catatgcaga acgtatttag ccattaccca cgtgacacca     2520
ccgaatatat tatcgattta gaagcaaaga tttcagtaga atttagtcc tgaacgctac        2580 ggggaaaatg cattttcttc agaattatcc attacgtgca tttaaactct gccagaaaaa      2640
aataactatt tgttttaat ctactttttg tatttagtag ttatttgtat aaattaaata       2700
aactgttttc aagtcaaaaa aaa                                               2724
```

-continued

```
<210> SEQ ID NO 4
<211> LENGTH: 509
<212> TYPE: PRT
<213> ORGANISM: Homo sapiens

<400> SEQUENCE: 4

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380
```

```
Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
                420                 425                 430

Asp Val Val Pro Asn Asp Pro Ser Phe Glu Asp Met Arg Lys Val Val
                435                 440                 445

Cys Val Asp Gln Gln Arg Pro Asn Ile Pro Asn Arg Trp Phe Ser Asp
        450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
                500                 505
```

<210> SEQ ID NO 5
<211> LENGTH: 2932
<212> TYPE: DNA
<213> ORGANISM: Homo sapiens

<400> SEQUENCE: 5

```
gctccgcgcc gagggctgga ggatgcgttc cctggggtcc ggacttatga aaatatgcat      60
cagtttaata ctgtcttgga attcatgaga tggaagcata ggtcaaagct gtttggagaa     120
aatcagaagt acagttttat ctagccacat cttggaggag tcgtaagaaa gcagtgggag     180
ttgaagtcat tgtcaagtgc ttgcgatctt ttacaagaaa atctcactga atgatagtca     240
tttaaattgg tgaagtagca agaccaatta ttaaaggtga cagtacacag gaaacattac     300
aattgaacaa tgactcagct atacatttac atcagattat tgggagccta tttgttcatc     360
atttctcgtg ttcaaggaca gaatctggat agtatgcttc atggcactgg gatgaaatca     420
gactccgacc agaaaaagtc agaaaatgga gtaaccttag caccagagga taccttgcct     480
tttttaaagt gctattgctc agggcactgt ccagatgatg ctattaataa cacatgcata     540
actaatggac attgctttgc catcatagaa gaagatgacc agggagaaac cacattagct     600
tcagggtgta tgaaatatga aggatctgat tttcagtgca aagattctcc aaaagcccag     660
ctacgccgga caatagaatg ttgtcggacc aatttatgta accagtattt gcaacccaca     720
ctgccccctg ttgtcatagg tccgtttttt gatggcagca ttcgatggct ggttttgctc     780
atttctatgg ctgtctgcat aattgctatg atcatcttct ccagctgctt ttgttacaaa     840
cattattgca agagcatctc aagcagacgt cgttacaatc gtgatttgga acaggatgaa     900
gcatttatt cagttggaga atcactaaaa gaccttattg accagtcaca aagttctggt     960
agtgggtctg gactaccttt attggttcag cgaactattg ccaaacagat tcagatggtc    1020
cggcaagttg gtaaaggccg atatggagaa gtatggatgg gcaaatggcg tggcgaaaaa    1080
gtggcggtga aagtattctt taccactgaa gaagccagct ggtttcgaga aacagaaatc    1140
taccaaactg tgctaatgcg ccatgaaaac atacttggtt tcatagcggc agacattaaa    1200
ggtacaggtt cctggactca gctctatttg attactgatt accatgaaaa tggatctctc    1260
tatgacttcc tgaaatgtgc tacactggac accagagccc tgcttaaatt ggcttattca    1320
gctgcctgtg gtctgtgcca cctgcacaca gaaatttatg gcacccaagg aaagcccgca    1380
attgctcatc gagacctaaa gagcaaaaac atcctcatca gaaaaatggg gagttgctgc    1440
```

-continued

```
attgctgacc tgggccttgc tgttaaattc aacagtgaca caaatgaagt tgatgtgccc    1500
ttgaatacca gggtgggcac caaacgctac atggctcccg aagtgctgga cgaaagcctg    1560
aacaaaaacc acttccagcc ctacatcatg gctgacatct acagcttcgg cctaatcatt    1620
tgggagatgg ctcgtcgttg tatcacagga gggatcgtgg aagaatacca attgccatat    1680
tacaacatgg taccgagtga tccgtcatac gaagatatgc gtgaggttgt gtgtgtcaaa    1740
cgtttgcggc caattgtgtc taatcggtgg aacagtgatg aatgtctacg agcagttttg    1800
aagctaatgt cagaatgctg ggcccacaat ccagcctcca gactcacagc attgagaatt    1860
aagaagacgc ttgccaagat ggttgaatcc aagatgtaa aaatctgatg gttaaaccat     1920
cggaggagaa actctagact gcaagaactg tttttaccca tggcatgggt ggaattagag    1980
tggaataagg atgttaactt ggttctcaga ctctttcttc actacgtgtt cacaggctgc    2040
taatattaaa cctttcagta ctcttattag gatacaagct gggaacttct aaacacttca    2100
ttctttatat atggacagct ttattttaaa tgtggttttt gatgcctttt tttaagtggg    2160
tttttatgaa ctgcatcaag acttcaatcc tgattagtgt ctccagtcaa gctctgggta    2220
ctgaattgcc tgttcataaa acggtgcttt ctgtgaaagc cttaagaaga taaatgagcg    2280
cagcagagat ggagaaatag actttgcctt ttacctgaga cattcagttc gtttgtattc    2340
tacctttgta aaacagccta tagatgatga tgtgtttggg atactgctta ttttatgata    2400
gtttgtcctg tgtccttagt gatgtgtgtg tgtctccatg cacatgcacg ccgggattcc    2460
tctgctgcca tttgaattag aagaaaataa tttatatgca tgcacaggaa gatattggtg    2520
gccggtggtt ttgtgcttta aaaatgcaat atctgaccaa gattcgccaa tctcatacaa    2580
gccatttact ttgcaagtga gatagcttcc ccaccagctt tatttttaa catgaaagct     2640 gatgccaagg ccaaaagaag tttaaagcat ctgtaaattt ggactgtttt ccttcaacca    2700 ccatttttt tgtggttatt attttttgtca cggaaagcat cctctccaaa gttggagctt    2760
ctattgccat gaaccatgct tacaaagaaa gcacttctta ttgaagtgaa ttcctgcatt    2820
tgatagcaat gtaagtgcct ataaccatgt tctatattct ttattctcag taacttttaa    2880
aagggaagtt atttatattt tgtgtataat gtgctttatt tgcaaatcac cc            2932
```

<210> SEQ ID NO 6
<211> LENGTH: 532
<212> TYPE: PRT
<213> ORGANISM: Homo sapiens

<400> SEQUENCE: 6

```
Met Thr Gln Leu Tyr Ile Tyr Ile Arg Leu Leu Gly Ala Tyr Leu Phe
 1               5                  10                  15

Ile Ile Ser Arg Val Gln Gly Gln Asn Leu Asp Ser Met Leu His Gly
            20                  25                  30

Thr Gly Met Lys Ser Asp Ser Asp Gln Lys Lys Ser Glu Asn Gly Val
        35                  40                  45

Thr Leu Ala Pro Glu Asp Thr Leu Pro Phe Leu Lys Cys Tyr Cys Ser
    50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Ala Ser Gly Cys Met Lys Tyr Glu Gly Ser Asp Phe Gln Cys Lys Asp
            100                 105                 110
```

-continued

```
Ser Pro Lys Ala Gln Leu Arg Arg Thr Ile Glu Cys Cys Arg Thr Asn
            115                 120                 125
Leu Cys Asn Gln Tyr Leu Gln Pro Thr Leu Pro Pro Val Val Ile Gly
        130                 135                 140
Pro Phe Phe Asp Gly Ser Ile Arg Trp Leu Val Leu Ile Ser Met
145                 150                 155                 160
Ala Val Cys Ile Ile Ala Met Ile Ile Phe Ser Ser Cys Phe Cys Tyr
                165                 170                 175
Lys His Tyr Cys Lys Ser Ile Ser Ser Arg Arg Tyr Asn Arg Asp
                180                 185                 190
Leu Glu Gln Asp Glu Ala Phe Ile Pro Val Gly Glu Ser Leu Lys Asp
            195                 200                 205
Leu Ile Asp Gln Ser Gln Ser Ser Gly Ser Gly Ser Gly Leu Pro Leu
        210                 215                 220
Leu Val Gln Arg Thr Ile Ala Lys Gln Ile Gln Met Val Arg Gln Val
225                 230                 235                 240
Gly Lys Gly Arg Tyr Gly Glu Val Trp Met Gly Lys Trp Arg Gly Glu
                245                 250                 255
Lys Val Ala Val Lys Val Phe Phe Thr Thr Glu Glu Ala Ser Trp Phe
                260                 265                 270
Arg Glu Thr Glu Ile Tyr Gln Thr Val Leu Met Arg His Glu Asn Ile
            275                 280                 285
Leu Gly Phe Ile Ala Ala Asp Ile Lys Gly Thr Gly Ser Trp Thr Gln
        290                 295                 300
Leu Tyr Leu Ile Thr Asp Tyr His Glu Asn Gly Ser Leu Tyr Asp Phe
305                 310                 315                 320
Leu Lys Cys Ala Thr Leu Asp Thr Arg Ala Leu Leu Lys Leu Ala Tyr
                325                 330                 335
Ser Ala Ala Cys Gly Leu Cys His Leu His Thr Glu Ile Tyr Gly Thr
            340                 345                 350
Gln Gly Lys Pro Ala Ile Ala His Arg Asp Leu Lys Ser Lys Asn Ile
        355                 360                 365
Leu Ile Lys Lys Asn Gly Ser Cys Cys Ile Ala Asp Leu Gly Leu Ala
        370                 375                 380
Val Lys Phe Asn Ser Asp Thr Asn Glu Val Asp Val Pro Leu Asn Thr
385                 390                 395                 400
Arg Val Gly Thr Lys Arg Tyr Met Ala Pro Glu Val Leu Asp Glu Ser
                405                 410                 415
Leu Asn Lys Asn His Phe Gln Pro Tyr Ile Met Ala Asp Ile Tyr Ser
            420                 425                 430
Phe Gly Leu Ile Ile Trp Glu Met Ala Arg Arg Cys Ile Thr Gly Gly
        435                 440                 445
Ile Val Glu Glu Tyr Gln Leu Pro Tyr Tyr Asn Met Val Pro Ser Asp
        450                 455                 460
Pro Ser Tyr Glu Asp Met Arg Glu Val Val Cys Val Lys Arg Leu Arg
465                 470                 475                 480
Pro Ile Val Ser Asn Arg Trp Asn Ser Asp Glu Cys Leu Arg Ala Val
                485                 490                 495
Leu Lys Leu Met Ser Glu Cys Trp Ala His Asn Pro Ala Ser Arg Leu
            500                 505                 510
Thr Ala Leu Arg Ile Lys Lys Thr Leu Ala Lys Met Val Glu Ser Gln
        515                 520                 525
```

Asp Val Lys Ile
    530

<210> SEQ ID NO 7
<211> LENGTH: 2333
<212> TYPE: DNA
<213> ORGANISM: Homo sapiens

<400> SEQUENCE: 7

| | | | | | |
|---|---|---|---|---|---|
| atggcggagt | cggccggagc | ctcctccttc | ttcccccttg | ttgtcctcct | gctcgccggc | 60 |
| agcggcgggt | ccgggccccg | gggggtccag | gctctgctgt | gtgcgtgcac | cagctgcctc | 120 |
| caggccaact | acacgtgtga | gacagatggg | gcctgcatgg | tttccttttt | caatctggat | 180 |
| gggatggagc | accatgtgcg | cacctgcatc | cccaaagtgg | agctggtccc | tgccgggaag | 240 |
| cccttctact | gcctgagctc | ggaggacctg | cgcaacaccc | actgctgcta | cactgactac | 300 |
| tgcaacagga | tcgacttgag | ggtgcccagt | ggtcacctca | aggagcctga | gcacccgtcc | 360 |
| atgtggggcc | cggtggagct | ggtaggcatc | atcgccggcc | cggtgttcct | cctgttcctc | 420 |
| atcatcatca | ttgttttcct | tgtcattaac | tatcatcagc | gtgtctatca | aaccgccag | 480 |
| agactggaca | tggaagatcc | ctcatgtgag | atgtgtctct | ccaaagacaa | gacgctccag | 540 |
| gatcttgtct | acgatctctc | cacctcaggg | tctggctcag | ggttacccct | ctttgtccag | 600 |
| cgcacagtgg | cccgaaccat | cgttttacaa | gagattattg | caagggtcg | gtttggggaa | 660 |
| gtatggcggg | gccgctggag | gggtggtgat | gtggctgtga | aaatattctc | ttctcgtgaa | 720 |
| gaacggtctt | ggttcaggga | agcagagata | taccagacgg | tcatgctgcg | ccatgaaaac | 780 |
| atccttggat | ttattgctgc | tgacaataaa | gataatggca | cctggacaca | gctgtggctt | 840 |
| gtttctgact | atcatgagca | cgggtccctg | tttgattatc | tgaaccggta | cacagtgaca | 900 |
| attgagggga | tgattaagct | ggccttgtct | gctgctagtg | ggctggcaca | cctgcacatg | 960 |
| gagatcgtgg | gcacccaagg | gaagcctgga | attgctcatc | gagacttaaa | gtcaaagaac | 1020 |
| attctggtga | agaaaaatgg | catgtgtgcc | atagcagacc | tgggcctggc | tgtccgtcat | 1080 |
| gatgcagtca | ctgacaccat | tgacattgcc | ccgaatcaga | gggtggggac | caaacgatac | 1140 |
| atggcccctg | aagtacttga | tgaaaccatt | aatatgaaac | actttgactc | ctttaaatgt | 1200 |
| gctgatattt | atgccctcgg | gcttgtatat | tgggagattg | ctcgaagatg | caattctgga | 1260 |
| ggagtccatg | aagaatatca | gctgccatat | tacgacttag | tgccctctga | cccttccatt | 1320 |
| gaggaaatgc | gaaaggttgt | atgtgatcag | aagctgcgtc | ccaacatccc | caactggtgg | 1380 |
| cagagttatg | aggcactgcg | ggtgatgggg | aagatgatgc | gagagtgttg | gtatgccaac | 1440 |
| ggcgcagccc | gcctgacggc | cctgcgcatc | aagaagaccc | tctcccagct | cagcgtgcag | 1500 |
| gaagacgtga | agatctaact | gctccctctc | tccacacgga | gctcctggca | gcgagaacta | 1560 |
| cgcacagctg | ccgcgttgag | cgtacgatgg | aggcctacct | ctcgtttctg | cccagccctc | 1620 |
| tgtggccagg | agccctggcc | cgcaagaggg | acagagcccg | ggagagactc | gctcactccc | 1680 |
| atgttgggtt | tgagacagac | accttttcta | tttacctcct | aatggcatgg | agactctgag | 1740 |
| agcgaattgt | gtggagaact | cagtgccaca | cctcgaactg | gttgtagtgg | gaagtcccgc | 1800 |
| gaaacccggt | gcatctggca | cgtggccagg | agccatgaca | ggggcgcttg | gagggggccg | 1860 |
| gaggaaccga | ggtgttgcca | gtgctaagct | gccctgaggg | tttccttcgg | ggaccagccc | 1920 |
| acagcacacc | aagtggggcc | ggaagaacca | gaagtgcagc | cctctcacag | gcagctctg | 1980 |
| agccgcgctt | tcccctcctc | cctgggatgg | acgctgccgg | gagactgcca | gtggagacgg | 2040 |

-continued

```
aatctgccgc tttgtctgtc cagccgtgtg tgcatgtgcc gaggtgcgtc ccccgttgtg    2100
cctggttcgt gccatgccct tacacgtgcg tgtgagtgtg tgtgtgtgtc tgtaggtgcg    2160
cacttacctg cttgagcttt ctgtgcatgt gcaggtcggg ggtgtggtcg tcatgctgtc    2220
cgtgcttgct ggtgcctctt ttcagtagtg agcagcatct agtttccctg gtgcccttcc    2280
ctggaggtct ctccctcccc cagagcccct catgccacag tggtactctg tgt           2333
```

<210> SEQ ID NO 8
<211> LENGTH: 505
<212> TYPE: PRT
<213> ORGANISM: Homo sapiens

<400> SEQUENCE: 8

```
Met Ala Glu Ser Ala Gly Ala Ser Ser Phe Phe Pro Leu Val Val Leu
1               5                   10                  15

Leu Leu Ala Gly Ser Gly Gly Ser Gly Pro Arg Gly Val Gln Ala Leu
            20                  25                  30

Leu Cys Ala Cys Thr Ser Cys Leu Gln Ala Asn Tyr Thr Cys Glu Thr
        35                  40                  45

Asp Gly Ala Cys Met Val Ser Phe Phe Asn Leu Asp Gly Met Glu His
    50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
            100                 105                 110

Leu Lys Glu Pro Glu His Pro Ser Met Trp Gly Pro Val Glu Leu Val
        115                 120                 125

Gly Ile Ile Ala Gly Pro Val Phe Leu Leu Phe Leu Ile Ile Ile Ile
    130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
        195                 200                 205

Leu Gln Glu Ile Ile Gly Lys Gly Arg Phe Gly Glu Val Trp Arg Gly
    210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Asp Asn
            260                 265                 270

Gly Thr Trp Thr Gln Leu Trp Leu Val Ser Asp Tyr His Glu His Gly
        275                 280                 285

Ser Leu Phe Asp Tyr Leu Asn Arg Tyr Thr Val Thr Ile Glu Gly Met
    290                 295                 300

Ile Lys Leu Ala Leu Ser Ala Ala Ser Gly Leu Ala His Leu His Met
305                 310                 315                 320

Glu Ile Val Gly Thr Gln Gly Lys Pro Gly Ile Ala His Arg Asp Leu
```

325                 330                 335
Lys Ser Lys Asn Ile Leu Val Lys Lys Asn Gly Met Cys Ala Ile Ala
                340                 345                 350
Asp Leu Gly Leu Ala Val Arg His Asp Ala Val Thr Asp Thr Ile Asp
                355                 360                 365
Ile Ala Pro Asn Gln Arg Val Gly Thr Lys Arg Tyr Met Ala Pro Glu
                370                 375                 380
Val Leu Asp Glu Thr Ile Asn Met Lys His Phe Asp Ser Phe Lys Cys
385                 390                 395                 400
Ala Asp Ile Tyr Ala Leu Gly Leu Val Tyr Trp Glu Ile Ala Arg Arg
                405                 410                 415
Cys Asn Ser Gly Gly Val His Glu Glu Tyr Gln Leu Pro Tyr Tyr Asp
                420                 425                 430
Leu Val Pro Ser Asp Pro Ser Ile Glu Glu Met Arg Lys Val Val Cys
                435                 440                 445
Asp Gln Lys Leu Arg Pro Asn Ile Pro Asn Trp Trp Gln Ser Tyr Glu
                450                 455                 460
Ala Leu Arg Val Met Gly Lys Met Met Arg Glu Cys Trp Tyr Ala Asn
465                 470                 475                 480
Gly Ala Ala Arg Leu Thr Ala Leu Arg Ile Lys Lys Thr Leu Ser Gln
                485                 490                 495
Leu Ser Val Gln Glu Asp Val Lys Ile
                500                 505

<210> SEQ ID NO 9
<211> LENGTH: 2308
<212> TYPE: DNA
<213> ORGANISM: Homo sapiens

<400> SEQUENCE: 9

```
ggcgaggcga ggtttgctgg ggtgaggcag cggcgcggcc gggccgggcc gggccacagg    60
cggtggcggc gggaccatgg aggcggcggt cgctgctccg cgtccccggc tgctcctcct   120
cgtgctggcg gcggcggcgg cggcggcggc ggcgctgctc ccggggggcga cggcgttaca   180
gtgtttctgc cacctctgta caaaagacaa ttttacttgt gtgacagatg ggctctgctt   240
tgtctctgtc acagagacca cagacaaagt tatacacaac agcatgtgta tagctgaaat   300
tgacttaatt cctcgagata ggccgttttgt atgtgcaccc tcttcaaaaa ctgggtctgt   360
gactacaaca tattgctgca atcaggacca ttgcaataaa atagaacttc caactactgt   420
aaagtcatca cctggccttg gtcctgtgga actggcagct gtcattgctg accagtgtg    480
cttcgtctgc atctcactca tgttgatggt ctatatctgc cacaaccgca ctgtcattca   540
ccatcgagtg ccaaatgaag aggacccttc attagatcgc ccttttattt cagagggtac   600
tacgttgaaa gacttaattt atgatatgac aacgtcaggt tctggctcag gtttaccatt   660
gcttgttcag agaacaattg cgagaactat tgtgttacaa gaaagcattg caaaggtcg    720
atttggagaa gtttggagag aaagtggcg gggagaagaa gttgctgtta agatattctc   780
ctctagagaa gaacgttcgt ggttccgtga ggcagagatt tatcaaactg taatgttacg   840
tcatgaaaac atcctgggat ttatagcagc agacaataaa gacaatggta cttggactca   900
gctctggttg gtgtcagatt atcatgagca tggatccctt tttgattact aaacagata    960
cacagttact gtggaaggaa tgataaaact tgctctgtcc acggcgagcg gtcttgccca  1020
tcttcacatg gagattgttg gtacccaagg aaagccagcc attgctcata gagatttgaa  1080
```

-continued

```
atcaaagaat atcttggtaa agaagaatgg aacttgctgt attgcagact taggactggc    1140
agtaagacat gattcagcca cagataccat tgatattgct ccaaaccaca gagtgggaac    1200
aaaaaggtac atggcccctg aagttctcga tgattccata aatatgaaac attttgaatc    1260
cttcaaacgt gctgacatct atgcaatggg cttagtattc tgggaaattg ctcgacgatg    1320
ttccattggt ggaattcatg aagattacca actgccttat tatgatcttg taccttctga    1380
cccatcagtt gaagaaatga gaaaagttgt ttgtgaacag aagttaaggc caaatatccc    1440
aaacagatgg cagagctgtg aagccttgag agtaatggct aaaattatga gagaatgttg    1500
gtatgccaat ggagcagcta ggcttacagc attgcggatt aagaaaacat tatcgcaact    1560
cagtcaacag gaaggcatca aaatgtaatt ctacagcttt gcctgaactc tcctttttc    1620 ttcagatctg ctcctgggtt ttaatttggg aggtcagttg ttctacctca ctgagaggga    1680
acagaaggat attgcttcct tttgcagcag tgtaataaag tcaattaaaa acttcccagg    1740
atttctttgg acccaggaaa cagccatgtg ggtcctttct gtgcactatg aacgcttctt    1800
tcccaggaca gaaaatgtgt agtctacctt tatttttat taacaaaact tgttttttaa    1860
aaagatgatt gctggtctta actttaggta actctgctgt gctggagatc atctttaagg    1920
gcaaaggagt tggattgctg aattacaatg aaacatgtct tattactaaa gaaagtgatt    1980
tactcctggt tagtacattc tcagaggatt ctgaaccact agagtttcct tgattcagac    2040
tttgaatgta ctgttctata gttttcagg atcttaaaac taacacttat aaaactctta    2100
tcttgagtct aaaaatgacc tcatatagta gtgaggaaca taattcatgc aattgtattt    2160
tgtatactat tattgttctt tcacttattc agaacattac atgccttcaa aatgggattg    2220
tactatacca gtaagtgcca cttctgtgtc tttctaatgg aaatgagtag aattgctgaa    2280
agtctctatg ttaaaaccta tagtgttt                                       2308
```

<210> SEQ ID NO 10
<211> LENGTH: 503
<212> TYPE: PRT
<213> ORGANISM: Homo sapiens

<400> SEQUENCE: 10

```
Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
    130                 135                 140

Val Tyr Ile Cys His Asn Arg Thr Val Ile His His Arg Val Pro Asn
145                 150                 155                 160
```

```
Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
        195                 200                 205

Glu Ser Ile Gly Lys Gly Arg Phe Gly Glu Val Trp Arg Gly Lys Trp
    210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
                260                 265                 270

Trp Thr Gln Leu Trp Leu Val Ser Asp Tyr His Glu His Gly Ser Leu
            275                 280                 285

Phe Asp Tyr Leu Asn Arg Tyr Thr Val Thr Val Glu Gly Met Ile Lys
        290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
                325                 330                 335

Lys Asn Ile Leu Val Lys Asn Gly Thr Cys Cys Ile Ala Asp Leu
                340                 345                 350

Gly Leu Ala Val Arg His Asp Ser Ala Thr Asp Thr Ile Asp Ile Ala
            355                 360                 365

Pro Asn His Arg Val Gly Thr Lys Arg Tyr Met Ala Pro Glu Val Leu
        370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
                420                 425                 430

Pro Ser Asp Pro Ser Val Glu Glu Met Arg Lys Val Val Cys Glu Gln
        435                 440                 445

Lys Leu Arg Pro Asn Ile Pro Asn Arg Trp Gln Ser Cys Glu Ala Leu
    450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
                485                 490                 495

Gln Gln Glu Gly Ile Lys Met
            500
```

<210> SEQ ID NO 11
<211> LENGTH: 1922
<212> TYPE: DNA
<213> ORGANISM: Mus musculus

<400> SEQUENCE: 11

```
gagagcacag cccttcccag tccccggagc cgccgcgcca cgcgcgcatg atcaagacct      60
tttccccggc cccacagggc tctggacgt gagacccegg ccgcctccgc aaggagaggc     120
```

-continued

```
ggggtcgag tcgccctgtc caaaggcctc aatctaaaca atcttgattc ctgttgccgg      180
ctggcgggac cctgaatggc aggaaatctc accacatctc ttctcctatc tccaaggacc      240
atgaccttgg ggagcttcag aagggccctt ttgatgctgt cggtggcctt gggcctaacc      300
caggggagac ttgcgaagcc ttccaagctg gtgaactgca cttgtgagag cccacactgc      360
aagagaccat tctgccaggg gtcatggtgc acagtggtgc tggttcgaga gcagggcagg      420
cacccccagg tctatcgggg ctgtgggagc ctgaaccagg agctctgctt gggacgtccc      480
acggagtttc tgaaccatca ctgctgctat agatccttct gcaaccacaa cgtgtctctg      540
atgctggagg ccacccaaac tccttcggag gagccagaag ttgatgccca tctgcctctg      600
atcctgggtc ctgtgctggc cttgccggtc ctggtggccc tgggtgctct gggcttgtgg      660
cgtgtccggc ggaggcagga aagcagcgg gatttgcaca gtgacctggg cgagtccagt      720
ctcatcctga aggcatctga acaggcagac agcatgttgg gggacttcct ggacagcgac      780
tgtaccacgg gcagcggctc ggggctcccc ttcttggtgc agaggacggt agctcggcag      840
gttgcgctgg tagagtgtgt gggaaagggc cgatatggcg aggtgtggcg cggttcgtgg      900
catggcgaaa gcgtggcggt caagattttc tcctcacgag atgagcagtc ctggttccgg      960
gagacggaga tctacaacac agttctgctt agacacgaca acatcctagg cttcatcgcc     1020
tccgacatga cttcgcggaa ctcgagcacg cagctgtggc tcatcaccca ctaccatgaa     1080
cacggctccc tctatgactt tctgcagagg cagacgctgg agcccagtt ggccctgagg      1140
ctagctgtgt ccccggcctg cggcctggcg cacctacatg tggagatctt tggcactcaa     1200
ggcaaaccag ccattgccca tcgtgacctc aagagtcgca atgtgctggt caagagtaac     1260
ttgcagtgtt gcattgcaga cctgggactg gctgtgatgc actcacaaag caacgagtac     1320
ctggatatcg gcaacacacc ccgagtgggt accaaaagat acatggcacc cgaggtgctg     1380
gatgagcaca tccgcacaga ctgctttgag tcgtacaagt ggacagacat ctgggccttt     1440
ggcctagtgc tatgggagat cgcccggcgg accatcatca tggcattgt ggaggattac      1500
aggccacctt tctatgacat ggtacccaat gaccccagtt ttgaggacat gaaaaaggtg     1560
gtgtgcgttg accagcagac acccaccatc cctaaccggc tggctgcaga tccggtcctc     1620
tccgggctgg cccagatgat gagagagtgc tggtacccca cccctctgc tcgcctcacc      1680
gcactgcgca taagaagac attgcagaag ctcagtcaca atccagagaa gcccaaagtg      1740
attcactagc ccagggccac caggcttcct ctgcctaaag tgtgtgctgg ggaagaagac     1800
atagcctgtc tgggtagagg gagtgaagag agtgtgcacg ctgccctgtg tgtgcctgct     1860
cagcttgctc ccagcccatc cagccaaaaa tacagctgag ctgaaattca aaaaaaaaa     1920
aa                                                                    1922
```

<210> SEQ ID NO 12
<211> LENGTH: 502
<212> TYPE: PRT
<213> ORGANISM: Mus musculus

<400> SEQUENCE: 12

```
Met Thr Leu Gly Ser Phe Arg Arg Gly Leu Leu Met Leu Ser Val Ala
1               5                   10                  15

Leu Gly Leu Thr Gln Gly Arg Leu Ala Lys Pro Ser Lys Leu Val Asn
            20                  25                  30

Cys Thr Cys Glu Ser Pro His Cys Lys Arg Pro Phe Cys Gln Gly Ser
        35                  40                  45
```

```
Trp Cys Thr Val Val Leu Val Arg Glu Gln Gly Arg His Pro Gln Val
     50                  55                  60
Tyr Arg Gly Cys Gly Ser Leu Asn Gln Glu Leu Cys Leu Gly Arg Pro
 65                  70                  75                  80
Thr Glu Phe Leu Asn His His Cys Cys Tyr Arg Ser Phe Cys Asn His
                 85                  90                  95
Asn Val Ser Leu Met Leu Glu Ala Thr Gln Thr Pro Ser Glu Glu Pro
            100                 105                 110
Glu Val Asp Ala His Leu Pro Leu Ile Leu Gly Pro Val Leu Ala Leu
            115                 120                 125
Pro Val Leu Val Ala Leu Gly Ala Leu Gly Leu Trp Arg Val Arg Arg
            130                 135                 140
Arg Gln Glu Lys Gln Arg Asp Leu His Ser Asp Leu Gly Glu Ser Ser
145                 150                 155                 160
Leu Ile Leu Lys Ala Ser Glu Gln Ala Asp Ser Met Leu Gly Asp Phe
                165                 170                 175
Leu Asp Ser Asp Cys Thr Thr Gly Ser Gly Ser Gly Leu Pro Phe Leu
            180                 185                 190
Val Gln Arg Thr Val Ala Arg Gln Val Ala Leu Val Glu Cys Val Gly
            195                 200                 205
Lys Gly Arg Tyr Gly Glu Val Trp Arg Gly Ser Trp His Gly Glu Ser
210                 215                 220
Val Ala Val Lys Ile Phe Ser Ser Arg Asp Glu Gln Ser Trp Phe Arg
225                 230                 235                 240
Glu Thr Glu Ile Tyr Asn Thr Val Leu Leu Arg His Asp Asn Ile Leu
                245                 250                 255
Gly Phe Ile Ala Ser Asp Met Thr Ser Arg Asn Ser Ser Thr Gln Leu
            260                 265                 270
Trp Leu Ile Thr His Tyr His Glu His Gly Ser Leu Tyr Asp Phe Leu
            275                 280                 285
Gln Arg Gln Thr Leu Glu Pro Gln Leu Ala Leu Arg Leu Ala Val Ser
            290                 295                 300
Pro Ala Cys Gly Leu Ala His Leu His Val Glu Ile Phe Gly Thr Gln
305                 310                 315                 320
Gly Lys Pro Ala Ile Ala His Arg Asp Leu Lys Ser Arg Asn Val Leu
                325                 330                 335
Val Lys Ser Asn Leu Gln Cys Cys Ile Ala Asp Leu Gly Leu Ala Val
            340                 345                 350
Met His Ser Gln Ser Asn Glu Tyr Leu Asp Ile Gly Asn Thr Pro Arg
            355                 360                 365
Val Gly Thr Lys Arg Tyr Met Ala Pro Glu Val Leu Asp Glu His Ile
            370                 375                 380
Arg Thr Asp Cys Phe Glu Ser Tyr Lys Trp Thr Asp Ile Trp Ala Phe
385                 390                 395                 400
Gly Leu Val Leu Trp Glu Ile Ala Arg Arg Thr Ile Ile Asn Gly Ile
                405                 410                 415
Val Glu Asp Tyr Arg Pro Pro Phe Tyr Asp Met Val Pro Asn Asp Pro
            420                 425                 430
Ser Phe Glu Asp Met Lys Lys Val Val Cys Val Asp Gln Gln Thr Pro
            435                 440                 445
Thr Ile Pro Asn Arg Leu Ala Ala Asp Pro Val Leu Ser Gly Leu Ala
            450                 455                 460
Gln Met Met Arg Glu Cys Trp Tyr Pro Asn Pro Ser Ala Arg Leu Thr
```

```
                465                 470                 475                 480
        Ala Leu Arg Ile Lys Lys Thr Leu Gln Lys Leu Ser His Asn Pro Glu
                            485                 490                 495
        Lys Pro Lys Val Ile His
                    500

<210> SEQ ID NO 13
<211> LENGTH: 2070
<212> TYPE: DNA
<213> ORGANISM: Mus musculus

<400> SEQUENCE: 13
attcatgaga tggaagcata ggtcaaagct gttcggagaa attggaacta cagttttatc      60
tagccacatc tctgagaatt ctgaagaaag cagcaggtga aagtcattgc caagtgattt     120
tgttctgtaa ggaagcctcc ctcattcact tacaccagtg agacagcagg accagtcatt     180
caaagggccg tgtacaggac gcgtggcaat cagacaatga ctcagctata cacttacatc     240
agattactgg gagcctgtct gttcatcatt tctcatgttc aagggcagaa tctagatagt     300
atgctccatg gcactggtat gaaatcagac ttggaccaga agaagccaga aaatggagtg     360
actttagcac cagaggatac cttgcctttc ttaaagtgct attgctcagg acactgccca     420
gatgatgcta ttaataacac atgcataact aatggccatt gctttgccat tatagaagaa     480
gatgatcagg gagaaaccac attaacttct gggtgtatga agtatgaagg ctctgatttt     540
caatgcaagg attcaccgaa agcccagcta cgcaggacaa tagaatgttg tcggaccaat     600
ttgtgcaacc agtatttgca gcctacactg ccccctgttg ttataggtcc gttctttgat     660
ggcagcatcc gatggctggt tgtgctcatt tccatggctg tctgtatagt tgctatgatc     720
atcttctcca gctgcttttg ctataagcat tattgtaaga gtatctcaag caggggtcgt     780
tacaaccgtg atttggaaca ggatgaagca tttattccag taggagaatc attgaaagac     840
ctgattgacc agtcccaaag ctctgggagt ggatctggat tgcctttatt ggttcagcga     900
actattgcca aacagattca gatggttcgg caggttgtaa aaggccgcta tggagaagta     960
tggatgggta atggcgtgtg tgaaaaagtg gctgtcaaag tgttttttac cactgaagaa    1020
gctagctggt ttagagaaac agaaatctac cagacggtgt taatgcgtca tgaaaatata    1080
cttggtttta tagctgcaga cattaaaggc actggttcct ggactcagct gtatttgatt    1140
actgattacc atgaaaatgg atctctctat gacttcctga atgtgccac actagacacc    1200
agagccctac tcaagttagc ttattctgct gcttgtggtc tgtgccacct ccacacagaa    1260
atttatggta cccaagggaa gcctgcaatt gctcatcgag acctgaagag caaaaacatc    1320
cttattaaga aaaatggaag ttgctgtatt gctgacctgg gcctagctgt taaattcaac    1380
agtgatacaa atgaagttga catacccttg aataccaggg tgggcaccaa gcggtacatg    1440
gctccagaag tgctggatga aagcctgaat aaaaaccatt tccagcccta catcatggct    1500
gacatctata gctttggttt gatcatttgg gaaatggctc gtcgttgtat tacaggagga    1560
atcgtggagg aatatcaatt accatattac aacatggtgc ccagtgaccc atcctatgag    1620
gacatgcgtg aggttgtgtg tgtgaaacgc ttgcggccaa tcgtgtctaa ccgctggaac    1680
agcgatgaat gtcttcgagc agttttgaag ctaatgtcag aatgttggc ccataatcca     1740
gcctccagac tcacagcttt gagaatcaag aagacacttg caaaaatggt tgaatcccag    1800
gatgtaaaga tttgacaatt aaacaatttt gagggagaat ttagactgca agaacttctt    1860
cacccaagga atgggtggga ttagcatgga ataggatgtt gacttggttt ccagactcct    1920
```

```
tcctctacat cttcacaggc tgctaacagt aaaccttacc gtactctaca gaatacaaga    1980
ttggaacttg gaacttcaaa catgtcattc tttatatatg acagctttgt tttaatgtgg    2040 ggttttttg tttgcttttt ttgttttgtt                                      2070
```

<210> SEQ ID NO 14
<211> LENGTH: 532
<212> TYPE: PRT
<213> ORGANISM: Mus musculus

<400> SEQUENCE: 14

```
Met Thr Gln Leu Tyr Thr Tyr Ile Arg Leu Leu Gly Ala Cys Leu Phe
 1               5                  10                  15

Ile Ile Ser His Val Gln Gly Gln Asn Leu Asp Ser Met Leu His Gly
             20                  25                  30

Thr Gly Met Lys Ser Asp Leu Asp Gln Lys Lys Pro Glu Asn Gly Val
         35                  40                  45

Thr Leu Ala Pro Glu Asp Thr Leu Pro Phe Leu Lys Cys Tyr Cys Ser
     50                  55                  60

Gly His Cys Pro Asp Asp Ala Ile Asn Asn Thr Cys Ile Thr Asn Gly
 65                  70                  75                  80

His Cys Phe Ala Ile Ile Glu Glu Asp Asp Gln Gly Glu Thr Thr Leu
                 85                  90                  95

Thr Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
    130                 135                 140

Pro Phe Phe Asp Gly Ser Ile Arg Trp Leu Val Val Leu Ile Ser Met
145                 150                 155                 160

Ala Val Cys Ile Val Ala Met Ile Ile Phe Ser Ser Cys Phe Cys Tyr
                165                 170                 175

Lys His Tyr Cys Lys Ser Ile Ser Ser Arg Gly Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
    290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
```

-continued

```
                         340                 345                 350
Gln Gly Lys Pro Ala Ile Ala His Arg Asp Leu Lys Ser Lys Asn Ile
        355                 360                 365
Leu Ile Lys Lys Asn Gly Ser Cys Cys Ile Ala Asp Leu Gly Leu Ala
370                 375                 380
Val Lys Phe Asn Ser Asp Thr Asn Glu Val Asp Ile Pro Leu Asn Thr
385                 390                 395                 400
Arg Val Gly Thr Lys Arg Tyr Met Ala Pro Glu Val Leu Asp Glu Ser
            405                 410                 415
Leu Asn Lys Asn His Phe Gln Pro Tyr Ile Met Ala Asp Ile Tyr Ser
                420                 425                 430
Phe Gly Leu Ile Ile Trp Glu Met Ala Arg Arg Cys Ile Thr Gly Gly
            435                 440                 445
Ile Val Glu Glu Tyr Gln Leu Pro Tyr Tyr Asn Met Val Pro Ser Asp
        450                 455                 460
Pro Ser Tyr Glu Asp Met Arg Glu Val Val Cys Val Lys Arg Leu Arg
465                 470                 475                 480
Pro Ile Val Ser Asn Arg Trp Asn Ser Asp Glu Cys Leu Arg Ala Val
                485                 490                 495
Leu Lys Leu Met Ser Glu Cys Trp Ala His Asn Pro Ala Ser Arg Leu
                500                 505                 510
Thr Ala Leu Arg Ile Lys Lys Thr Leu Ala Lys Met Val Glu Ser Gln
            515                 520                 525
Asp Val Lys Ile
    530
```

<210> SEQ ID NO 15
<211> LENGTH: 2160
<212> TYPE: DNA
<213> ORGANISM: Mus musculus

<400> SEQUENCE: 15

| | | | | | |
|---|---|---|---|---|---|
| cgcggttaca | tggcggagtc | ggccggagcc | tcctccttct | tccccttgt | tgtcctcctg | 60 |
| ctcgccggca | gcggcgggtc | cgggccccgg | gggatccagg | ctctgctgtg | tgcgtgcacc | 120 |
| agctgcctac | agaccaacta | cacctgtgag | acagatgggg | cttgcatggt | ctccatcttt | 180 |
| aacctggatg | gcgtggagca | ccatgtacgt | acctgcatcc | caaggtgga | gctggttcct | 240 |
| gctggaaagc | ccttctactg | cctgagttca | gaggatctgc | gcaacacaca | ctgctgctat | 300 |
| attgacttct | gcaacaagat | tgacctcagg | gtccccagcg | acacctcaa | ggagcctgcg | 360 |
| cacccctcca | tgtggggccc | tgtggagctg | gtcggcatca | tcgccggccc | cgtcttcctc | 420 |
| ctcttcctta | tcattatcat | cgtcttcctg | gtcatcaact | atcaccagcg | tgtctaccat | 480 |
| aaccgccaga | ggttggacat | ggaggacccc | tcttgcgaga | tgtgtctctc | caaagacaag | 540 |
| acgctccagg | atctcgtcta | cgacctctcc | acgtcagggt | ctggctcagg | ttacccctt | 600 |
| tttgtccagc | gcacagtggc | ccgaaccatt | gttttacaag | agattatcgg | caagggccgg | 660 |
| tcggggaag | tatggcgtgg | tcgctggagg | ggtggtgacg | tggctgtgaa | aatcttctct | 720 |
| tctcgtgaag | aacggtcttg | gttccgtgaa | gcagagatct | accagaccgt | catgctgcgc | 780 |
| catgaaaaca | tccttggctt | tattgctgct | gacaataaag | ataatggcac | ctggacccag | 840 |
| ctgtggcttg | tctctgacta | tcacgagcat | ggctcactgt | ttgattatct | gaaccgctac | 900 |
| acagtgacca | ttgagggaat | gattaagcta | gccttgtctg | cagccagtgg | tttggcacac | 960 |
| ctgcatatgg | agattgtggg | cactcaaggg | aagccgggaa | ttgctcatcg | agacttgaag | 1020 |

-continued

```
tcaaagaaca tcctggtgaa aaaaaatggc atgtgtgcca ttgcagacct gggcctggct      1080
gtccgtcatg atgcggtcac tgacaccata gacattgctc caaatcagag ggtggggacc      1140
aaacgataca tggctcctga agtccttgac gagacaatca acatgaagca ctttgactcc      1200
ttcaaatgtg ccgacatcta tgccctcggg cttgtctact gggagattgc acgaagatgc      1260
aattctggag gagtccatga agactatcaa ctgccgtatt acgacttagt gccctccgac      1320
ccttccattg aggagatgcg aaaggttgta tgtgaccaga agctacggcc caatgtcccc      1380
aactggtggc agagttatga ggccttgcga gtgatgggaa agatgatgcg ggagtgctgg      1440
tacgccaatg gtgctgcccg tctgacagct ctgcgcatca agaagactct gtcccagcta      1500
agcgtgcagg aagatgtgaa gatttaagct gttcctctgc ctacacaaag aacctgggca      1560
gtgaggatga ctgcagccac cgtgcaagcg tcgtggaggc ctatcctctt gtttctgccc      1620
ggccctctgg cagagccctg gcctgcaaga gggacagagc tgggagacg cgcgcactcc      1680 cgttgggttt gagacagaca cttttatat ttacctcctg atggcatgga gacctgagca      1740
aatcatgtag tcactcaatg ccacaactca aactgcttca gtgggaagta cagagaccca      1800
gtgcattgcg tgtgcaggag cgtgaggtgc tgggctcgcc aggagcggcc cccatacctt      1860
gtggtccact gggctgcagg ttttcctcca gggaccagtc aactggcatc aagatattga      1920
gaggaaccgg aagtttctcc ctccttcccg tagcagtcct gagccacacc atccttctca      1980
tggacatccg gaggactgcc cctagagaca caacctgctg cctgtctgtc cagccaagtg      2040
cgcatgtgcc gaggtgtgtc ccacattgtg cctggtctgt gccacgcccg tgtgtgtgtg      2100
tgtgtgtgtg agtgagtgtg tgtgtgtaca cttaacctgc ttgagcttct gtgcatgtgt      2160
```

<210> SEQ ID NO 16
<211> LENGTH: 505
<212> TYPE: PRT
<213> ORGANISM: Mus musculus

<400> SEQUENCE: 16

```
Met Ala Glu Ser Ala Gly Ala Ser Ser Phe Phe Pro Leu Val Val Leu
1               5                   10                  15

Leu Leu Ala Gly Ser Gly Gly Ser Gly Pro Arg Gly Ile Gln Ala Leu
            20                  25                  30

Leu Cys Ala Cys Thr Ser Cys Leu Gln Thr Asn Tyr Thr Cys Glu Thr
        35                  40                  45

Asp Gly Ala Cys Met Val Ser Ile Phe Asn Leu Asp Gly Val Glu His
    50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Ile Asp Phe Cys Asn Lys Ile Asp Leu Arg Val Pro Ser Gly His
            100                 105                 110

Leu Lys Glu Pro Ala His Pro Ser Met Trp Gly Pro Val Glu Leu Val
        115                 120                 125

Gly Ile Ile Ala Gly Pro Val Phe Leu Leu Phe Leu Ile Ile Ile Ile
    130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175
```

```
Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
        195                 200                 205

Leu Gln Glu Ile Ile Gly Lys Gly Arg Phe Gly Glu Val Trp Arg Gly
    210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Asp Asn
            260                 265                 270

Gly Thr Trp Thr Gln Leu Trp Leu Val Ser Asp Tyr His Glu His Gly
        275                 280                 285

Ser Leu Phe Asp Tyr Leu Asn Arg Tyr Thr Val Thr Ile Glu Gly Met
    290                 295                 300

Ile Lys Leu Ala Leu Ser Ala Ala Ser Gly Leu Ala His Leu His Met
305                 310                 315                 320

Glu Ile Val Gly Thr Gln Gly Lys Pro Gly Ile Ala His Arg Asp Leu
                325                 330                 335

Lys Ser Lys Asn Ile Leu Val Lys Lys Asn Gly Met Cys Ala Ile Ala
            340                 345                 350

Asp Leu Gly Leu Ala Val Arg His Asp Ala Val Thr Asp Thr Ile Asp
        355                 360                 365

Ile Ala Pro Asn Gln Arg Val Gly Thr Lys Arg Tyr Met Ala Pro Glu
    370                 375                 380

Val Leu Asp Glu Thr Ile Asn Met Lys His Phe Asp Ser Phe Lys Cys
385                 390                 395                 400

Ala Asp Ile Tyr Ala Leu Gly Leu Val Tyr Trp Glu Ile Ala Arg Arg
                405                 410                 415

Cys Asn Ser Gly Gly Val His Glu Asp Tyr Gln Leu Pro Tyr Tyr Asp
            420                 425                 430

Leu Val Pro Ser Asp Pro Ser Ile Glu Glu Met Arg Lys Val Val Cys
        435                 440                 445

Asp Gln Lys Leu Arg Pro Asn Val Pro Asn Trp Trp Gln Ser Tyr Glu
    450                 455                 460

Ala Leu Arg Val Met Gly Lys Met Met Arg Glu Cys Trp Tyr Ala Asn
465                 470                 475                 480

Gly Ala Ala Arg Leu Thr Ala Leu Arg Ile Lys Lys Thr Leu Ser Gln
                485                 490                 495

Leu Ser Val Gln Glu Asp Val Lys Ile
            500                 505

<210> SEQ ID NO 17
<211> LENGTH: 1952
<212> TYPE: DNA
<213> ORGANISM: Mus musculus

<400> SEQUENCE: 17
aagcggcggc agaagttgcc ggcgtggtgc tcgtagtgag ggcgcggagg acccgggacc      60
tgggaagcgg cggcgggtta acttcggctg aatcacaacc atttggcgct gagctatgac     120
aagagagcaa acaaaaagtt aaaggagcaa cccggccata agtgaagaga aagtttatt      180 gataacatgc tcttacgaag ctctggaaaa ttaaatgtgg gcaccaagaa ggaggatgga     240
```

-continued

```
gagagtacag ccccccacccc tcggcccaag atcctacgtt gtaaatgcca ccaccactgt    300
ccggaagact cagtcaacaa tatctgcagc acagatgggt actgcttcac gatgatagaa    360
gaagatgact ctggaatgcc tgttgtcacc tctggatgtc taggactaga agggtcagat    420
tttcaatgtc gtgacactcc cattcctcat caaagaagat caattgaatg ctgcacagaa    480
aggaatgagt gtaataaaga cctccacccc actctgcctc ctctcaagga cagagatttt    540
gttgatgggc ccatacacca caaggccttg cttatctctg tgactgtctg tagtttactc    600
ttggtcctca ttattttatt ctgttacttc aggtataaaa gacaagaagc ccgacctcgg    660
tacagcattg ggctggagca ggacgagaca tacattcctc ctggagagtc cctgagagac    720
ttgatcgagc agtctcagag ctcgggaagt ggatcaggcc tccctctgct ggtccaaagg    780
acaatagcta agcaaattca gatggtgaag cagattggaa aaggccgcta tggcgaggtg    840
tggatgggaa agtggcgtgg agaaaaggtg gctgtgaaag tgttcttcac cacggaggaa    900
gccagctggt tccgagagac tgagatatat cagacggtcc tgatgcggca tgagaatatt    960
ctggggttca ttgctgcaga tatcaaaggg actgggtcct ggactcagtt gtacctcatc   1020
acagactatc atgaaaacgg ctcccttttat gactatctga atccaccac cttagacgca   1080
aagtccatgc tgaagctagc ctactcctct gtcagcggcc tatgccattt acacacggaa   1140
atctttagca ctcaaggcaa gccagcaatc gcccatcgag acttgaaaag taaaaacatc   1200
ctggtgaaga aaaatggaac ttgctgcata gcagacctgg gcttggctgt caagttcatt   1260
agtgacacaa atgaggttga catcccaccc aacacccggg ttggcaccaa gcgctatatg   1320
cctccagaag tgctggacga gagcttgaat agaaaccatt tccagtccta cattatggct   1380
gacatgtaca gctttggact catcctctgg gagattgcaa ggagatgtgt ttctggaggt   1440
atagtggaag aataccagct tccctatcac gacctggtgc ccagtgaccc ttcttatgag   1500
gacatgagag aaattgtgtg catgaagaag ttacggcctt cattccccaa tcgatggagc   1560
agtgatgagt gtctcaggca gatggggaag cttatgacag agtgctgggc gcagaatcct   1620
gcctccaggc tgacggccct gagagttaag aaaacccttg ccaaaatgtc agagtcccag   1680
gacattaaac tctgacgtca gatacttgtg gacagagcaa gaatttcaca gaagcatcgt   1740
tagcccaagc cttgaacgtt agcctactgc ccagtgagtt cagactttcc tggaagagag   1800
cacggtgggc agacacagag gaacccagaa cacggattc atcatggctt tctgaggagg   1860
agaaactgtt tgggtaactt gttcaagata tgatgcatgt tgctttctaa gaaagccctg   1920
tattttgaat taccattttt ttataaaaaa aa                                  1952
```

<210> SEQ ID NO 18
<211> LENGTH: 502
<212> TYPE: PRT
<213> ORGANISM: Mus musculus

<400> SEQUENCE: 18

Met Leu Leu Arg Ser Ser Gly Lys Leu Asn Val Gly Thr Lys Lys Glu
1               5                   10                  15

Asp Gly Glu Ser Thr Ala Pro Thr Pro Arg Pro Lys Ile Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Asp Ser Gly Met
    50                  55                  60

```
Pro Val Val Thr Ser Gly Cys Leu Gly Leu Glu Gly Ser Asp Phe Gln
 65                  70                  75                  80

Cys Arg Asp Thr Pro Ile Pro His Gln Arg Arg Ser Ile Glu Cys Cys
                 85                  90                  95

Thr Glu Arg Asn Glu Cys Asn Lys Asp Leu His Pro Thr Leu Pro Pro
                100                 105                 110

Leu Lys Asp Arg Asp Phe Val Asp Gly Pro Ile His His Lys Ala Leu
            115                 120                 125

Leu Ile Ser Val Thr Val Cys Ser Leu Leu Val Leu Ile Ile Leu
        130                 135                 140

Phe Cys Tyr Phe Arg Tyr Lys Arg Gln Glu Ala Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
                260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
        290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
            340                 345                 350

Leu Ala Val Lys Phe Ile Ser Asp Thr Asn Glu Val Asp Ile Pro Pro
        355                 360                 365

Asn Thr Arg Val Gly Thr Lys Arg Tyr Met Pro Pro Glu Val Leu Asp
370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Ile Ala Arg Arg Cys Val Ser
                405                 410                 415

Gly Gly Ile Val Glu Glu Tyr Gln Leu Pro Tyr His Asp Leu Val Pro
                420                 425                 430

Ser Asp Pro Ser Tyr Glu Asp Met Arg Glu Ile Val Cys Met Lys Lys
        435                 440                 445

Leu Arg Pro Ser Phe Pro Asn Arg Trp Ser Ser Asp Glu Cys Leu Arg
        450                 455                 460

Gln Met Gly Lys Leu Met Thr Glu Cys Trp Ala Gln Asn Pro Ala Ser
465                 470                 475                 480

Arg Leu Thr Ala Leu Arg Val Lys Lys Thr Leu Ala Lys Met Ser Glu
```

```
              485                 490                 495
Ser Gln Asp Ile Lys Leu
            500
```

<210> SEQ ID NO 19
<211> LENGTH: 28
<212> TYPE: DNA
<213> ORGANISM: Artificial Sequence
<220> FEATURE:
<223> OTHER INFORMATION: Sense primer, extracellular domain.
<220> FEATURE:
<221> NAME/KEY: misc_feature
<222> LOCATION: (20)..(20)
<223> OTHER INFORMATION: The nucleotide at position 20 may be any
      nucleotide <400> SEQUENCE: 19
gcggatcctg ttgtgaaggn aatatgtg                                    28

<210> SEQ ID NO 20
<211> LENGTH: 24
<212> TYPE: DNA
<213> ORGANISM: Artificial Sequence
<220> FEATURE:
<223> OTHER INFORMATION: Sense primer, kinase domain II
<400> SEQUENCE: 20
gcgatccgtc gcagtcaaaa tttt                                        24

<210> SEQ ID NO 21
<211> LENGTH: 26
<212> TYPE: DNA
<213> ORGANISM: Artificial Sequence
<220> FEATURE:
<223> OTHER INFORMATION: Sense Primer, Kinase domain VIB
<400> SEQUENCE: 21
gcggatccgc gatatattaa aagcaa                                      26

<210> SEQ ID NO 22
<211> LENGTH: 20
<212> TYPE: DNA
<213> ORGANISM: Artificial sequence
<220> FEATURE:
<223> OTHER INFORMATION: Anti-sense primer, Kinase Domain VIB
<400> SEQUENCE: 22
cggaattctg gtgccatata                                             20

<210> SEQ ID NO 23
<211> LENGTH: 37
<212> TYPE: DNA
<213> ORGANISM: Artificial Sequence
<220> FEATURE:
<223> OTHER INFORMATION: Oligonucleotide probe
<400> SEQUENCE: 23
attcaagggc acatcaactt catttgtgtc actgttg                          37

<210> SEQ ID NO 24
<211> LENGTH: 26
<212> TYPE: DNA
<213> ORGANISM: Artificial Sequence
<220> FEATURE:
<223> OTHER INFORMATION: 5' Oligonucleotide primer
<400> SEQUENCE: 24

-continued

```
gcggatccac catggcggag tcggcc                                            26

<210> SEQ ID NO 25
<211> LENGTH: 20
<212> TYPE: DNA
<213> ORGANISM: Artificial sequence
<220> FEATURE:
<223> OTHER INFORMATION: 3' Oligonucleotide primer

<400> SEQUENCE: 25
aacaccgggc cggcgatgat                                                   20

<210> SEQ ID NO 26
<211> LENGTH: 6
<212> TYPE: PRT
<213> ORGANISM: Artificial Sequence
<220> FEATURE:
<223> OTHER INFORMATION: Consensus sequence in Subdomain I
<220> FEATURE:
<221> NAME/KEY: MISC_FEATURE
<222> LOCATION: (2)..(2)
<223> OTHER INFORMATION: Xaa at position 2 may be any amino acid
<220> FEATURE:
<221> NAME/KEY: MISC_FEATURE
<222> LOCATION: (4)..(5)
<223> OTHER INFORMATION: Xaa at position 4 and 5 may be any amino acid

<400> SEQUENCE: 26

Gly Xaa Gly Xaa Xaa Gly
1               5

<210> SEQ ID NO 27
<211> LENGTH: 6
<212> TYPE: PRT
<213> ORGANISM: Homo sapiens

<400> SEQUENCE: 27

Asp Phe Lys Ser Arg Asn
1               5

<210> SEQ ID NO 28
<211> LENGTH: 6
<212> TYPE: PRT
<213> ORGANISM: Homo sapiens

<400> SEQUENCE: 28

Asp Leu Lys Ser Lys Asn
1               5

<210> SEQ ID NO 29
<211> LENGTH: 6
<212> TYPE: PRT
<213> ORGANISM: Homo sapiens

<400> SEQUENCE: 29

Gly Thr Lys Arg Tyr Met
1               5

<210> SEQ ID NO 30
<211> LENGTH: 182
<212> TYPE: PRT
<213> ORGANISM: Homo sapiens

<400> SEQUENCE: 30

Leu Asp Thr Leu Val Gly Lys Gly Arg Phe Ala Glu Val Tyr Lys Ala
1               5                   10                  15
```

Lys Leu Lys Gln Asn Thr Ser Glu Gln Phe Glu Thr Val Ala Val Lys
           20                  25                  30

Ile Phe Pro Tyr Asp His Tyr Ala Ser Trp Lys Asp Arg Lys Asp Ile
           35                  40                  45

Phe Ser Asp Ile Asn Leu Lys His Glu Asn Ile Leu Gln Phe Leu Thr
       50                  55                  60

Ala Glu Glu Arg Lys Thr Glu Leu Gly Lys Gln Tyr Trp Leu Ile Thr
65                  70                  75                  80

Ala Phe His Ala Lys Gly Asn Leu Gln Glu Tyr Leu Thr Arg His Val
               85                  90                  95

Ile Ser Trp Glu Asp Leu Arg Asn Val Gly Ser Ser Leu Ala Arg Gly
           100                 105                 110

Leu Ser His Leu His Ser Asp His Thr Pro Cys Gly Arg Pro Lys Met
           115                 120                 125

Pro Ile Val His Arg Asp Leu Lys Ser Ser Asn Ile Leu Val Lys Asn
           130                 135                 140

Asp Leu Thr Cys Cys Leu Cys Asp Phe Gly Leu Ser Leu Arg Leu Gly
145                 150                 155                 160

Pro Tyr Ser Ser Val Asp Asp Leu Ala Asn Ser Gly Gln Val Gly Thr
               165                 170                 175

Ala Arg Tyr Met Ala Pro
               180

<210> SEQ ID NO 31
<211> LENGTH: 176
<212> TYPE: PRT
<213> ORGANISM: Mus musculus

<400> SEQUENCE: 31

Leu Leu Glu Ile Lys Ala Arg Gly Arg Phe Gly Cys Val Trp Lys Ala
1               5                   10                  15

Gln Leu Met Asn Asp Phe Val Ala Val Lys Ile Phe Pro Leu Gln Asp
           20                  25                  30

Lys Gln Ser Trp Gln Ser Glu Arg Glu Ile Phe Ser Thr Pro Gly Met
           35                  40                  45

Lys His Glu Asn Leu Leu Gln Phe Ile Ala Ala Glu Lys Arg Gly Ser
       50                  55                  60

Asn Leu Glu Val Glu Leu Trp Leu Ile Thr Ala Phe His Asp Lys Gly
65                  70                  75                  80

Ser Leu Thr Asp Tyr Leu Lys Gly Asn Ile Ile Thr Trp Asn Glu Leu
               85                  90                  95

Cys His Val Ala Glu Thr Met Ser Arg Gly Leu Ser Tyr Leu His Glu
           100                 105                 110

Asp Val Pro Trp Cys Arg Gly Glu Gly His Lys Pro Ser Ile Ala His
           115                 120                 125

Arg Asp Phe Lys Ser Lys Asn Val Leu Leu Lys Ser Asp Leu Thr Ala
           130                 135                 140

Val Leu Ala Asp Phe Gly Leu Ala Val Arg Phe Glu Pro Gly Lys Pro
145                 150                 155                 160

Pro Gly Asp Thr His Gly Gln Val Gly Thr Arg Arg Tyr Met Ala Pro
               165                 170                 175

<210> SEQ ID NO 32
<211> LENGTH: 175
<212> TYPE: PRT

<213> ORGANISM: Mus musculus

<400> SEQUENCE: 32

```
Leu Leu Glu Val Lys Ala Arg Gly Arg Phe Gly Cys Val Trp Lys Ala
1               5                   10                  15

Gln Leu Leu Asn Glu Tyr Val Ala Val Lys Ile Phe Pro Ile Gln Asp
            20                  25                  30

Lys Gln Ser Trp Gln Asn Glu Tyr Glu Val Tyr Ser Leu Pro Gly Met
        35                  40                  45

Lys His Glu Asn Ile Leu Gln Phe Ile Gly Ala Glu Lys Arg Gly Thr
    50                  55                  60

Ser Val Asp Val Asp Leu Trp Leu Ile Thr Ala Phe His Glu Lys Gly
65                  70                  75                  80

Ser Leu Ser Asp Phe Leu Lys Ala Asn Val Val Ser Trp Asn Glu Leu
                85                  90                  95

Cys His Ile Ala Glu Thr Met Ala Arg Gly Leu Ala Tyr Leu His Glu
            100                 105                 110

Asp Ile Pro Gly Leu Lys Asp Gly His Lys Pro Ala Ile Ser His Arg
        115                 120                 125

Asp Ile Lys Ser Lys Asn Val Leu Leu Lys Asn Asn Leu Thr Ala Cys
    130                 135                 140

Ile Ala Asp Phe Gly Leu Ala Leu Lys Phe Glu Ala Gly Lys Ser Ala
145                 150                 155                 160

Gly Asp Thr His Gly Gln Val Gly Thr Arg Arg Tyr Met Ala Pro
                165                 170                 175
```

<210> SEQ ID NO 33
<211> LENGTH: 178
<212> TYPE: PRT
<213> ORGANISM: Caenorhabditis elegans

<400> SEQUENCE: 33

```
Leu Thr Gly Arg Val Gly Ser Gly Arg Phe Gly Asn Val Ser Arg Gly
1               5                   10                  15

Asp Tyr Arg Gly Glu Ala Val Ala Val Lys Val Phe Asn Ala Leu Asp
            20                  25                  30

Glu Pro Ala Phe His Lys Glu Thr Glu Ile Phe Glu Thr Arg Met Leu
        35                  40                  45

Arg His Pro Asn Val Leu Arg Tyr Ile Gly Ser Asp Arg Val Asp Thr
    50                  55                  60

Gly Phe Val Thr Glu Leu Trp Leu Val Thr Glu Tyr His Pro Ser Gly
65                  70                  75                  80

Ser Leu His Asp Phe Leu Leu Glu Asn Thr Val Asn Ile Glu Thr Tyr
                85                  90                  95

Tyr Asn Leu Met Arg Ser Thr Ala Ser Gly Leu Ala Phe Leu His Asn
            100                 105                 110

Gln Ile Gly Gly Ser Lys Glu Ser Asn Lys Pro Ala Met Ala His Arg
        115                 120                 125

Asp Ile Lys Ser Lys Asn Ile Met Val Lys Asn Asp Leu Thr Cys Ala
    130                 135                 140

Ile Gly Asp Leu Gly Leu Ser Leu Ser Lys Pro Glu Asp Ala Ala Ser
145                 150                 155                 160

Asp Ile Ile Ala Asn Glu Asn Tyr Lys Cys Gly Thr Val Arg Tyr Leu
                165                 170                 175

Ala Pro
```

```
<210> SEQ ID NO 34
<211> LENGTH: 513
<212> TYPE: PRT
<213> ORGANISM: Mus musculus

<400> SEQUENCE: 34

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
```

```
            370                 375                 380
Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
            435                 440                 445

Ala Gly Met Ala Met Leu Cys Glu Thr Ile Glu Glu Cys Trp Asp His
        450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
            500                 505                 510

Leu

<210> SEQ ID NO 35
<211> LENGTH: 536
<212> TYPE: PRT
<213> ORGANISM: Mus musculus

<400> SEQUENCE: 35

Met Thr Ala Pro Trp Ala Ala Leu Ala Leu Leu Trp Gly Ser Leu Cys
1               5                   10                  15

Ala Gly Ser Gly Arg Gly Glu Ala Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Val Arg
                165                 170                 175

Gln Cys Gln Arg Trp Ala Gly Arg Arg Asp Gly Cys Ala Asp Ser Phe
            180                 185                 190

Lys Pro Leu Pro Phe Gln Asp Pro Gly Pro Pro Pro Ser Pro Leu
        195                 200                 205

Val Gly Leu Lys Pro Leu Gln Leu Leu Glu Ile Lys Ala Arg Gly Arg
    210                 215                 220

Phe Gly Cys Val Trp Lys Ala Gln Leu Met Asn Asp Phe Val Ala Val
```

```
                  225                 230                 235                 240
Lys Ile Phe Pro Leu Gln Asp Lys Gln Ser Trp Gln Ser Glu Arg Glu
                245                 250                 255

Ile Phe Ser Thr Pro Gly Met Lys His Glu Asn Leu Leu Gln Phe Ile
                260                 265                 270

Ala Ala Glu Lys Arg Gly Ser Asn Leu Glu Val Glu Leu Trp Leu Ile
                275                 280                 285

Thr Ala Phe His Asp Lys Gly Ser Leu Thr Asp Tyr Leu Lys Gly Asn
                290                 295                 300

Ile Ile Thr Trp Asn Glu Leu Cys His Val Ala Glu Thr Met Ser Arg
305                 310                 315                 320

Gly Leu Ser Tyr Leu His Glu Asp Val Pro Trp Cys Arg Gly Glu Gly
                325                 330                 335

His Lys Pro Ser Ile Ala His Arg Asp Phe Lys Ser Lys Asn Val Leu
                340                 345                 350

Leu Lys Ser Asp Leu Thr Ala Val Leu Ala Asp Phe Gly Leu Ala Val
                355                 360                 365

Arg Phe Glu Pro Gly Lys Pro Pro Gly Asp Thr His Gly Gln Val Gly
                370                 375                 380

Thr Arg Arg Tyr Met Ala Pro Glu Val Leu Glu Gly Ala Ile Asn Phe
385                 390                 395                 400

Gln Arg Asp Ala Phe Leu Arg Ile Asp Met Tyr Ala Met Gly Leu Val
                405                 410                 415

Leu Trp Glu Leu Val Ser Arg Cys Lys Ala Ala Asp Gly Pro Val Asp
                420                 425                 430

Glu Tyr Met Leu Pro Phe Glu Glu Ile Gly Gln His Pro Ser Leu
                435                 440                 445

Glu Glu Leu Gln Glu Val Val Val His Lys Lys Met Arg Pro Thr Ile
                450                 455                 460

Lys Asp His Trp Leu Lys His Pro Gly Leu Ala Gln Leu Cys Val Thr
465                 470                 475                 480

Ile Glu Glu Cys Trp Asp His Asp Ala Glu Ala Arg Leu Ser Ala Gly
                485                 490                 495

Cys Val Glu Glu Arg Val Ser Leu Ile Arg Arg Ser Val Asn Gly Thr
                500                 505                 510

Thr Ser Asp Cys Leu Val Ser Leu Val Thr Ser Val Thr Asn Val Asp
                515                 520                 525

Leu Leu Pro Lys Glu Ser Ser Ile
                530                 535

<210> SEQ ID NO 36
<211> LENGTH: 567
<212> TYPE: PRT
<213> ORGANISM: Homo sapiens

<400> SEQUENCE: 36

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
                35                  40                  45

Gln Leu Cys Lys Phe Cys Asp Val Arg Phe Ser Thr Cys Asp Asn Gln
                50                  55                  60
```

-continued

```
Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                 85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Phe Tyr Cys Tyr Arg Val Asn
                180                 185                 190

Arg Gln Gln Lys Leu Ser Ser Thr Trp Glu Thr Gly Lys Thr Arg Lys
                195                 200                 205

Leu Met Glu Phe Ser Glu His Cys Ala Ile Ile Leu Glu Asp Asp Arg
            210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
                260                 265                 270

Thr Val Ala Val Lys Ile Phe Pro Tyr Glu Glu Tyr Ala Ser Trp Lys
            275                 280                 285

Thr Glu Lys Asp Ile Phe Ser Asp Ile Asn Leu Lys His Glu Asn Ile
            290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
            355                 360                 365

Gly Arg Pro Lys Met Pro Ile Val His Arg Asp Leu Lys Ser Ser Asn
370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
                420                 425                 430

Arg Met Asn Leu Glu Asn Ala Glu Ser Phe Lys Gln Thr Asp Val Tyr
            435                 440                 445

Ser Met Ala Leu Val Leu Trp Glu Met Thr Ser Arg Cys Asn Ala Val
            450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
```

```
                       485                 490                 495
Arg Pro Glu Ile Pro Ser Phe Trp Leu Asn His Gln Gly Ile Gln Met
                500                 505                 510

Val Cys Glu Thr Leu Thr Glu Cys Trp Asp His Asp Pro Glu Ala Arg
            515                 520                 525

Leu Thr Ala Gln Cys Val Ala Glu Arg Phe Ser Glu Leu Glu His Leu
        530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 37
<211> LENGTH: 97
<212> TYPE: PRT
<213> ORGANISM: Caenorhabditis elegans

<400> SEQUENCE: 37

Cys His Cys Ser Arg Glu Val Gly Cys Asn Ala Arg Thr Thr Gly Trp
1               5                   10                  15

Val Pro Gly Ile Glu Phe Leu Asn Glu Thr Asp Arg Ser Phe Tyr Glu
            20                  25                  30

Asn Thr Cys Tyr Thr Asp Gly Ser Cys Tyr Gln Ser Ala Arg Pro Ser
        35                  40                  45

Pro Glu Ile Ser His Phe Gly Cys Met Asp Glu Lys Ser Val Thr Asp
    50                  55                  60

Glu Thr Glu Phe His Asp Thr Ala Ala Lys Val Cys Thr Asn Asn Thr
65                  70                  75                  80

Lys Asp Pro His Ala Thr Val Trp Ile Cys Cys Asp Lys Gly Asn Phe
                85                  90                  95

Cys

<210> SEQ ID NO 38
<211> LENGTH: 6
<212> TYPE: PRT
<213> ORGANISM: Artificial Sequence
<220> FEATURE:
<223> OTHER INFORMATION: Serine/threonine kinase consensus

<400> SEQUENCE: 38

Asp Leu Lys Pro Glu Asn
1               5

<210> SEQ ID NO 39
<211> LENGTH: 6
<212> TYPE: PRT
<213> ORGANISM: Artificial Sequence
<220> FEATURE:
<223> OTHER INFORMATION: Tyrosine kinase consensus

<400> SEQUENCE: 39

Asp Leu Ala Ala Arg Asn
1               5

<210> SEQ ID NO 40
<211> LENGTH: 6
<212> TYPE: PRT
<213> ORGANISM: Artificial Sequence
<220> FEATURE:
<223> OTHER INFORMATION: Act R-II motif
```

```
<400> SEQUENCE: 40

Asp Ile Lys Ser Lys Asn
1               5

<210> SEQ ID NO 41
<211> LENGTH: 6
<212> TYPE: PRT
<213> ORGANISM: Artificial Sequence
<220> FEATURE:
<223> OTHER INFORMATION: Act R-IIB motif

<400> SEQUENCE: 41

Asp Phe Lys Ser Lys Asn
1               5

<210> SEQ ID NO 42
<211> LENGTH: 6
<212> TYPE: PRT
<213> ORGANISM: Artificial Sequence
<220> FEATURE:
<223> OTHER INFORMATION: TaR-II motif

<400> SEQUENCE: 42

Asp Leu Lys Ser Ser Asn
1               5

<210> SEQ ID NO 43
<211> LENGTH: 6
<212> TYPE: PRT
<213> ORGANISM: Artificial Sequence
<220> FEATURE:
<223> OTHER INFORMATION: Artificial Peptide
<220> FEATURE:
<221> NAME/KEY: MISC_FEATURE
<222> LOCATION: (2)..(2)
<223> OTHER INFORMATION: Xaa at position 2 is Thr or Ser
<220> FEATURE:
<221> NAME/KEY: MISC_FEATURE
<222> LOCATION: (3)..(4)
<223> OTHER INFORMATION: Xaa at position three and four can be any amino
      acid
<220> FEATURE:
<221> NAME/KEY: MISC_FEATURE
<222> LOCATION: (5)..(5)
<223> OTHER INFORMATION: Xaa at position five is Tyr or Phe
<220> FEATURE:
<221> NAME/KEY: MISC_FEATURE
<222> LOCATION: (6)..(6)
<223> OTHER INFORMATION: Xaa at position six may be any amino acid

<400> SEQUENCE: 43

Gly Xaa Xaa Xaa Xaa Xaa
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is any amino acid
<220> FEATURE:
<221> NAME/KEY: MISC_FEATURE
<222> LOCATION: (3)..(3)
<223> OTHER INFORMATION: Xaa at position 3 is Ile or Val
<220> FEATURE:
<221> NAME/KEY: MISC_FEATURE
<222> LOCATION: (4)..(4)
```

```
<223> OTHER INFORMATION: Xaa at position 4 is Lys or Arg
<220> FEATURE:
<221> NAME/KEY: MISC_FEATURE
<222> LOCATION: (6)..(6)
<223> OTHER INFORMATION: Xaa at position 6 is Thr or Met.

<400> SEQUENCE: 44

Xaa Pro Xaa Xaa Trp Xaa
1               5

<210> SEQ ID NO 45
<211> LENGTH: 6
<212> TYPE: PRT
<213> ORGANISM: Homo sapiens

<400> SEQUENCE: 45

Gly Thr Arg Arg Tyr Met
1               5

<210> SEQ ID NO 46
<211> LENGTH: 6
<212> TYPE: PRT
<213> ORGANISM: Homo sapiens

<400> SEQUENCE: 46

Gly Thr Ala Arg Tyr Met
1               5
```